(12) United States Patent
Prakash et al.

(10) Patent No.: US 9,029,335 B2
(45) Date of Patent: May 12, 2015

(54) SUBSTITUTED 2'-THIO-BICYCLIC NUCLEOSIDES AND OLIGOMERIC COMPOUNDS PREPARED THEREFROM

(71) Applicant: Isis Pharmaceuticals, Inc., Carlsbad, CA (US)

(72) Inventors: Thazha P. Prakash, Carlsbad, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 33 days.

(21) Appl. No.: 14/049,450

(22) Filed: Oct. 9, 2013

(65) Prior Publication Data

US 2014/0106451 A1  Apr. 17, 2014

Related U.S. Application Data

(60) Provisional application No. 61/714,307, filed on Oct. 16, 2012.

(51) Int. Cl.

| | | |
|---|---|---|
| *A01N 43/04* | (2006.01) | |
| *A61K 31/70* | (2006.01) | |
| *C12N 15/113* | (2010.01) | |
| *C07H 19/10* | (2006.01) | |
| *C07H 19/207* | (2006.01) | |
| *C07H 19/06* | (2006.01) | |
| *C07H 19/16* | (2006.01) | |
| *C07H 19/20* | (2006.01) | |

(52) U.S. Cl.
CPC .............. *C12N 15/113* (2013.01); *C07H 19/10* (2013.01); *C07H 19/207* (2013.01); *C07H 19/06* (2013.01); *C07H 19/16* (2013.01); *C07H 19/20* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. | |
| 4,415,732 A | 11/1983 | Caruthers et al. | |
| 4,458,066 A | 7/1984 | Caruthers et al. | |
| 4,469,863 A | 9/1984 | Ts'o et al. | |
| 4,476,301 A | 10/1984 | Imbach et al. | |
| 4,500,707 A | 2/1985 | Caruthers et al. | |
| 4,668,777 A | 5/1987 | Caruthers et al. | |
| 4,725,677 A | 2/1988 | Koster et al. | |
| 4,845,205 A | 7/1989 | Huynh Dinh et al. | |
| 4,973,679 A | 11/1990 | Caruthers et al. | |
| 4,981,957 A | 1/1991 | Lebleu et al. | |
| 5,013,830 A | 5/1991 | Ohutsuka et al. | |
| 5,023,243 A | 6/1991 | Tullis | |
| 5,034,506 A | 7/1991 | Summerton et al. | |
| 5,118,800 A | 6/1992 | Smith et al. | |
| 5,130,302 A | 7/1992 | Spielvogel et al. | |
| 5,132,418 A | 7/1992 | Caruthers et al. | |
| 5,134,066 A | 7/1992 | Rogers et al. | |
| RE34,036 E | 8/1992 | McGeehan | |
| 5,149,797 A | 9/1992 | Pederson et al. | |
| 5,166,315 A | 11/1992 | Summerton et al. | |
| 5,175,273 A | 12/1992 | Bischofberger et al. | |
| 5,177,196 A | 1/1993 | Meyer, Jr. et al. | |
| 5,177,198 A | 1/1993 | Spielvogel et al. | |
| 5,185,444 A | 2/1993 | Summerton et al. | |
| 5,188,897 A | 2/1993 | Suhadolnik et al. | |
| 5,194,599 A | 3/1993 | Froehler | |
| 5,214,134 A | 5/1993 | Weis et al. | |
| 5,216,141 A | 6/1993 | Benner | |
| 5,220,007 A | 6/1993 | Pederson et al. | |
| 5,223,618 A | 6/1993 | Cook et al. | |
| 5,235,033 A | 8/1993 | Summerton et al. | |
| 5,256,775 A | 10/1993 | Froehler | |
| 5,264,423 A | 11/1993 | Cohen et al. | |
| 5,264,562 A | 11/1993 | Matteucci | |
| 5,264,564 A | 11/1993 | Matteucci | |
| 5,276,019 A | 1/1994 | Cohen et al. | |
| 5,278,302 A | 1/1994 | Caruthers et al. | |
| 5,286,717 A | 2/1994 | Cohen et al. | |
| 5,319,080 A | 6/1994 | Leumann | |
| 5,321,131 A | 6/1994 | Agrawal et al. | |
| 5,359,044 A | 10/1994 | Cook et al. | |
| 5,366,878 A | 11/1994 | Pederson et al. | |
| 5,367,066 A | 11/1994 | Urdea et al. | |

(Continued)

FOREIGN PATENT DOCUMENTS

| | | |
|---|---|---|
| WO | WO 94/02499 | 2/1994 |
| WO | WO 94/17093 | 8/1994 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — Patrick Lewis
(74) *Attorney, Agent, or Firm* — Casimir Jones, S.C.

(57) ABSTRACT

Provided herein are novel bicyclic nucleosides, oligomeric compounds that include such bicyclic nucleosides and methods of using the oligomeric compounds. More particularly, the novel bicyclic nucleosides comprise a furanose ring system having a bridge comprising a 4'-methylene group attached to a 2'-sulfoxide or sulfone group and optionally including one or more substituent groups attached to the 4'-methylene and or the 5'-position. In certain embodiments, the oligomeric compounds provided herein are expected to hybridize to a portion of a target RNA resulting in loss of normal function of the target RNA.

26 Claims, No Drawings

(56) References Cited

U.S. PATENT DOCUMENTS

| | | | |
|---|---|---|---|
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,426,220 B1 | 7/2002 | Bennett et al. |
| 6,525,191 B1 | 2/2003 | Ramasamy |
| 6,600,032 B1 | 7/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,867,294 B1 | 3/2005 | Sanghvi et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 7,741,457 B2 | 6/2010 | Seth et al. |
| 2003/0082807 A1 | 5/2003 | Wengel |
| 2003/0087230 A1 | 5/2003 | Wengel |
| 2003/0158403 A1 | 8/2003 | Manoharan et al. |
| 2003/0207841 A1 | 11/2003 | Kaneko et al. |
| 2003/0224377 A1 | 12/2003 | Wengel et al. |
| 2004/0014959 A1 | 1/2004 | Sorensen et al. |
| 2004/0143114 A1 | 7/2004 | Imanishi et al. |
| 2004/0192918 A1 | 9/2004 | Imanishi et al. |
| 2004/0219565 A1 | 11/2004 | Kauppinen et al. |
| 2004/0241717 A1 | 12/2004 | Hansen et al. |
| 2005/0130923 A1 | 6/2005 | Bhat et al. |
| 2008/0039618 A1 | 2/2008 | Allerson et al. |

FOREIGN PATENT DOCUMENTS

| | | |
|---|---|---|
| WO | WO 98/39352 | 9/1998 |
| WO | WO 99/14226 | 3/1999 |
| WO | WO 01/49687 | 7/2001 |
| WO | WO 02/36743 | 5/2002 |
| WO | WO 2004/069992 | 8/2004 |
| WO | WO 2004/106356 | 12/2004 |
| WO | WO 2005/021570 | 3/2005 |
| WO | WO 2005/121371 | 12/2005 |
| WO | WO 2005/121372 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2010/036696 | 4/2010 |

OTHER PUBLICATIONS

Altmann et al., "Second-generation antisense oligonucleotides: structure-activity relationships and the design of improved signal-transduction inhibitors" Biochem. Soc. Trans. (1996) 24:630-637.

Altmann et al., "Second Generation of Antisense Oligonucleotides: From Nuclease Resistance to Biological Efficacy in Animals" Chimia (1996) 50(4):168-176.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16(7-9):917-926.

Baker et al., "2'-O-(2 Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bass, "Double-stranded RNA as a template for gene silencing" Cell (2000) 101:235-238.

(56) References Cited

OTHER PUBLICATIONS

Beaucage et al., "Advances in the Synthesis of Oligonucleotides by the Phosphoramidite Approach" Tetrahedron (1992) 48(12):2223-2311.
Beaucage et al., "The Functionalization of Oligonucleotides Via Phosphoramidite Derivatives" Tetrahedron (1993) 49(10):1925-1963.
Beaucage et al., "The Synthesis of Specific Ribonucleotides and Unrelated Phosphorylated Biomolecules by the Phosphoramidite Method" Tetrahedron (1993) 49(46):10441-10488.
Beigelman et al., "Alternate Approaches to the Synthesis of 2'-O-Me Nucleosides" Nucleosides and Nucleotides (1995), 14(3-5): 901-905.
Belikova et al., "Synthesis of Ribonucleosides and Diribonucleoside Phosphates Containing 2-Chloro-Ethylamine and Nitrogen Mustard Residues" Tet. Lett. (1967) 37:3557-3562.
Braasch et al., "Locked nucleic acid (LNA): fine-tuning the recognition of DNA and RNA" Chem. Biol. (2001) 8:1-7.
Elayadi et al., "Application of PNA and LNA oligomers to chemotherapy" Curr. Opinion Invens. Drugs (2001) 2:558-561.
Elbashir, "Duplexes of 21-nucleotide RNAs mediate RNA interference in cultured mammalian cells" Nature (2001) 411:494-498.
Elbashir, "RNA interference is mediated by 21- and 22-nucleotide RNAs" Genes & Devel. (2001) 15:188-200.
Englisch et al., "Chemically Modified Oligonucleotides as Probes and Inhibitors" Agnew Chem. Int. Ed. Engl. (1991) 30:613-629.
Fire et al., "Potent and Specific Genetic Interference by Double-Stranded RNA in *Caenorhabditis elegans*" Nature (1998) 391:806-811.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Fluiter et al., "On the in vitro and in vivo Properties of Four Locked Nucleic Acid Nucleotides Incorporated into an Anti-H-Ras Antisense Oligonucleotide" ChemBioChem (2005) 6: 1104-1109.
Gu et al., "Base Pairing Properties of D- and L-Cyclohexene Nucleic Acids (CeNA)" Oligonucleotides (2003) 13(6): 479-489.
Gu et al., "Synthesis of enantiomeric-pure cyclohexenyl nucleoside building blocks for oligonucleotide synthesis" Tetrahedron (2004) 60(9): 2111-2123.
Gu et al., "Enzymatic Resolution and Base Pairing Properties of D- and L-Cyclohexenyl Nucleic Acids (CeNA)" Nucleosides, Nucleotides & Nucleic Acids (2005) 24(5-7): 993-998.
Horvath et al., "Stereoselective synthesis of ( )-ara-cyclohexenyl-adenine" Tetrahedron Letters (2007) 48: 3621-3623.
Jin et al., "Stereoselective Synthesis of Dithymidine Phosphorothioates Using Xylose Derivatives as Chiral Auxiliaries" J. Org. Chem. (1998) 63: 3647-3654.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Leumann et al., "DNA Analogues: From Supramolecular Principles to Biological Properties" Bioorganic & Medicinal Chemistry (2002) 10:841-854.

Martin, "Ein neuer Zugang zu 2'-O-Alkylribonucleosiden and Eigenschaften deren Oligonucleotide" Helv. Chim. Acta (1995) 78:486-504.
Mikhailov et al., "Substrate Properties of C'-Methylnucleoside and C'-Methyl-2"-Deoxynucleoside 5'Triphosphates in RNA and DNA Synthesis Reactions Catalysed by RNA and DNA Polymerases" Nucleosides & Nucleotides (1991) 10(1-3):339-343.
Montgomery et al., "RNA as a target of double-stranded RNA-mediated genetic interference in *Caenorhabditis elegans*" Proc Natl. Acad. Sci. (1998) 95:15502-7.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
Nauwelaerts et al., "Cyclohexenyl nucleic acids: conformationally flexible oligonucleotides" Nucleic Acids Research (2005) 33(8): 2452-2463.
Nishikura et al., "A Short Primer on RNAi: RNA-Directed RNA Polymerase Acts as a Key Catalyst" Cell (2001) 107:415-418.
Orum et al., "Locked nucleic acids: A promising molecular family for gene-function analysis and antisense drug development" Curr. Opinion Mol. Ther. (2001) 3:239-243.
Pederson et al., "Analogues of LNA (Locked Nucleic Acid): Synthesis of the 2'-Thio-LNA Ribothymidine and 5-Methylcytidine Phosphoramidites" Synthesis (2004) 4: 578-582.
Robeyns et al., "Oligonucleotides with cyclohexene-nucleoside building blocks: crystallization and preliminary X-ray studies of a left-handed sequence GTGTACAC" Acta Crystallographica, Section F: Structural Biology and Crystallization Communications (2005) F61(6): 585-586.
Robeyns et al., "Structure of the Fully Modified Left-Handed Cyclohexene Nucleic Acid Sequence GTGTACAC" J. Am. Chem. Soc. (2008) 130(6): 1979-1984.
Saha et al., "5'-Me-DNA—A New Oligonucleotide Analog: Synthesis and Biochemical Properties" J. Org. Chem. (1995) 60:788-789.
Sanghvi, Chapter 15, Antisense Research and Applications, Crooke and Lebleu ed., CRC Press (1993).
Scaringe, "RNA Oligonucleotide Synthesis via 5'-Silyl-2'-Orthoester Chemistry" Methods (2001) 23:206-217.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Singh et al., "Synthesis of Novel Bicyclo Ribonucleosides: 2'-Amino- and 2'-Thio-LNA Monomeric Nucleosides" Journal of Organic Chemistry (1998) 63(18), 6078-6079.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Swayze et al., The Medicinal Chemistry of Oligonucleotides in Antisense Drug Technology 2nd edition, Chapter 6, pp. 143-182 (Crooke, S.T., ed., 2008).
Tabara et al., "RNAi in *C. elegans*: Soaking in the Genome Sequence" Science (1998) 282:430-431.
Tusterman et al., "RNA hellcase MUT-14-dependent gene silencing triggered in *C. elegans* by short antisense RNAs" Science (2002) 295:694-7.
Timmons et al., "Ingestion of bacterially expressed dsRNAs can produce specific and potent genetic interference in *Caenorhabditis elegans*" Gene (2001) 263:103-112.
Timmons et al., "Specific Interference by Ingested dsRNA" Nature (1998) 395:854.
Tuschl et al., "Targeted mRNA degradation by double-stranded RNA in vitro" Genes Dev. (1999) 13:3191-7.
Verbeure et al., "RNase H mediated cleavage of RNA by cyclohexene nucleic acid (CeNA)" Nucleic Acids Research (2001) 29(24): 4941-4947.
Wahlestedt et al., "Potent and nontoxic antisense oligonucleotide containing locked nucleic acids" Proc. Natl. Acad. Sci. USA (2000) 97: 5633-5638.

(56) References Cited

OTHER PUBLICATIONS

Wang et al., "Biophysical and biochemical properties of oligodeoxynucleotides containing 4'-C- and 5'-C-substituted thymidines" Bioorganic & Medicinal Chemistry Letters (1999) 9(6): 885-890.

Wang et al., "Cyclohexene Nucleic Acids (CeNA): Serum Stable Oligonucleotides that Activate RNase H and Increase Duplex Stability with Complementary RNA" J. Am. Chem. Soc.(2000) 122: 8595-8602.

Wang et al., "A Straightforward Stereoselective Synthesis of D- and L-5-Hydroxy-4-hydroxymethyl-2-cyclohexenylguanine" J. Org. Chem. (2001) 66: 8478-8482.

Wang et al., "Stereocontrolled Synthesis of Ara-Type Cyclohexenyl Nucleosides" J. Org. Chem. (2003) 68: 4499-4505.

Wang et al., "Cyclohexene Nucleic Acids (CeNA) Form Stable Duplexes With RNA and Induce RNase H Activity" Nucleosides, Nucleotides & Nucleic Acids (2001) 20(4-7): 785-788.

Wang et al., "A stereoselective synthesis of dinucleotide phosphorothioates, using chiral indol-oxazaphosphorine intermediates" Tetrahedron Letters (1997) 38(22): 3797-3800.

Wang et al., "A stereoselective synthesis of dinucleotide phosphorothioate triesters through a chiral indol-oxazaphosphorine intermediate" Tetrahedron Letters (1997) 38(5): 705-708.

Zamecnik et al., "Inhibition of Rous sarcoma virus replication and cell transformation by a specific oligodeoxynucleotide" PNAS (1978) 75:280-284.

SEQUENCE LISTING

<160> NUMBER OF SEQ ID NOS: 6

<210> SEQ ID NO 1
<211> LENGTH: 3160
<212> TYPE: DNA
<213> ORGANISM: H. sapeins

<400> SEQUENCE: 1

```
cctcccctcg cccggcgcgg tcccgtccgc ctctcgctcg cctcccgcct ccccctcggtc      60
ttccgaggcg cccgggctcc cggcgcggcg gcggaggggg cggcaggcc ggcgggcggt       120
gatgtggcag gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga     300
gcccctctca gcgcctgtga gcagccgcgg gggcagcgcc ctcggggagc cggccggcct      360
gcggcggcg cagcggcggc gtttctcgcc tcctcttcgt cttttctaac cgtgcagcct       420
cttcctcggc ttctcctgaa agggaaggtg gaagccgtgg gctcgggcgg gagccggctg     480
aggcgcggcg gcggcggcgg cggcacctcc cgctcctgga gcgggggga gaagcggcgg      540
cggcggcggc cgcggcggct gcagctccag ggaggggtc tgagtcgcct gtcaccattt       600
ccagggctgg gaacgccgga gagttggtct ctcccttct actgcctcca acacggcggc      660
ggcggcggcg gcacatccag ggacccgggc cggttttaaa cctcccgtcc gccgccgccg      720
cacccccgt ggcccgggct ccggaggccg ccggcggagg cagccgttcg gaggattatt       780
cgtcttctcc ccattccgct gccgccgctg ccaggcctct ggctgctgag gagaagcagg     840
cccagtcgct gcaaccatcc agcagccgcc gcagcagcca ttacccggct gcggtccaga     900
gccaagcggc ggcagagcga gggcatcag ctaccgccaa gtccagagcc atttccatcc      960
tgcagaagaa gccccgccac cagcagcttc tgccatctct ctcctccttt ttcttcagcc    1020
acaggctccc agacatgaca gccatcatca agagatcgt tagcagaaac aaaaggagat    1080
atcaagagga tggattcgac ttagacttga cctatattta tccaaacatt attgctatgg    1140
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caatttaat tgcagagttg cacaatatcc ttttgaagac cataacccac     1320
cacagctaga acttatcaaa cccttttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaattttt taaaggcaca agaggcccta gatttctatg    1500
gggaagtaag gaccagagac aaaaagggag taactattcc cagtcagagg cgctatgtgt    1560
attattatag ctacctgtta aagaatcatc tggattatag accagtggca ctgttgtttc    1620
```

```
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt ttttttatca agagggataa aacaccatga    2280
aaataaactt gaataaactg aaaatggacc tttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460 tatataccxt tttgtgtcaa aaggacattt aaaattcaat taggattaat aaagatggca    2520
ctttcccgtt ttattccagt tttataaaaa gtggagacag actgatgtgt atacgtagga    2580 atttttcct tttgtgttct gtcaccaact gaagtggcta aagagctttg tgatatactg    2640
gttcacatcc tacccctttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160
```

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                          26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                           25

<210> SEQ ID NO 4

```
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                    30

<210> SEQ ID NO 5
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 5
agcaaaaaac gc                                                       12

<210> SEQ ID NO 6
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 6
gcgttttttg ct                                                       12
```

SUBSTITUTED 2'-THIO-BICYCLIC NUCLEOSIDES AND OLIGOMERIC COMPOUNDS PREPARED THEREFROM

RELATED APPLICATIONS

This application claims priority under 35 U.S.C. §119(e) to U.S. Provisional Patent Application No. 61/714,307, filed Oct. 16, 2012, which is incorporated herein by reference in its entirety.

SEQUENCE LISTING

The present application is being filed along with a Sequence Listing in electronic format. The Sequence Listing is provided as a file entitled CHEM0060USSEQ.TXT, created Oct. 7, 2012, which is 8 Kb in size. The information in the electronic format of the sequence listing is incorporated herein by reference in its entirety.

FIELD OF THE INVENTION

Provided herein are novel bicyclic nucleosides, oligomeric compounds that include such bicyclic nucleosides and methods of using the oligomeric compounds. More particularly, the novel bicyclic nucleosides comprise a furanose ring system having a bridge comprising an optionally substituted 4'-methylene group attached to a 2'-sulfoxide or sulfone group and optionally including one or more substituent groups attached to the 5'-position. In certain embodiments, the oligomeric compounds provided herein are expected to hybridize to a portion of a target RNA resulting in loss of normal function of the target RNA. The oligomeric compounds provided herein are also expected to be useful as primers and probes in diagnostic applications.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various bicyclic nucleosides have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8(16), 2219-2222; Wengel et al., PCT International Application number PCT/DK98/00393 (published as WO 99/14226 on Mar. 25, 1999), filed Sep. 14, 1998; Singh et al., J. Org. Chem., 1998, 63, 10035-10039, the text of each is incorporated by reference herein, in their entirety. Examples of issued US patents and published applications include for example: U.S. Pat. Nos. 6,770,748, 6,268,490 and 6,794,499 and published U.S. applications 20040219565, 20040014959, 20030207841, 20040192918, 20030224377, 20040143114, 20030087230 and 20030082807, the text of each is incorporated by reference herein, in their entirety.

The synthesis of 5'-substituted DNA and RNA derivatives and their incorporation into oligomeric compounds has been reported in the literature (see for example: Saha et al., J. Org. Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343) and Leonid et al., 1995, 14(3-5), 901-905).

The synthesis of 2'-thio bicyclic nucleosides has been reported in the literature (see for example: International Application PCT/DK98/00393 ibid; International Application PCT/DK-2004/000097, filed Feb. 10, 2004, and published as WO 2004/069992 on Aug. 19, 2004; Singh et al., Journal of Organic Chemistry, 1998, 63(18), 6078-6079; Pedersen et al., Synthesis, 2004, 4, 578-582; U.S. Application 20040014959, published Jan. 22, 2004; and U.S. Application 2004241717, published Dec. 2, 2004).

The synthesis of 2'-Thio bicyclic nucleosides and their incorporation into oligomeric compounds has been reported in the literature. Selected oligonucleotides have been looked at for evaluation of Tm, in vitro activity and in vivo activity (see for example: Kumar ibid; and Fluiter et al., *ChemBioChem*, 2005, 6, 1-6).

There remains a long-felt need for agents that specifically regulate gene expression via antisense mechanisms. Disclosed herein are oligomeric compounds such as antisense compounds useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are novel bicyclic nucleosides, oligomeric compounds that include such bicyclic nucleosides and methods of using the oligomeric compounds. More particularly, the novel bicyclic nucleosides comprise a furanose ring system having a bridge comprising an optionally substituted 4'-methylene group attached to a 2'-sulfoxide or sulfone group and optionally including one or more substituent groups attached to the 5'-position. The variables are defined individually in further detail herein. It is to be understood that the substituted 2'-thio bicyclic nucleosides and oligomeric compounds provided herein include all combinations of the embodiments disclosed and variables defined herein.

In certain embodiments, bicyclic nucleosides are provided having Formula Ia:

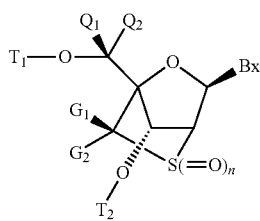

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each substituted group is, independently, mono or poly substituted with substituent groups independently selected from halogen, $OJ_1$, $SJ_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=O)NJ_1J_2$ and $N(H)C(=S)NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
n is 1 or 2.

In certain embodiments, Bx is an optionally protected pyrimidine, substituted pyrimidine, purine or substituted purine. In certain embodiments, Bx is uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine In certain embodiments, at least one of $Q_1$, $Q_2$, $G_1$ and $G_2$ is $CH_3$ and the remaining of $Q_1$, $Q_2$, $G_1$ and $G_2$ are each H. In certain embodiments, $Q_1$, $Q_2$, $G_1$ and $G_2$ are each H.

In certain embodiments, $T_1$ is 4,4'-dimethoxytrityl and $T_2$ is diisopropylcyanoethoxy phosphoramidite.

In certain embodiments, n is 1 and the configuration at the sulfur atom is R. In certain embodiments, n is 1 and the configuration at the sulfur atom is S. In certain embodiments, n is 2.

In certain embodiments, $Q_1$, $Q_2$, $G_1$ and $G_2$ are each H, $T_1$ is 4,4'-dimethoxytrityl and $T_2$ is diisopropylcyanoethoxy phosphoramidite.

In certain embodiments, oligomeric compounds are provided comprising at least one bicyclic nucleoside of Formula IIa:

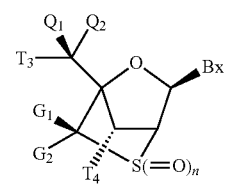

wherein independently for each bicyclic nucleoside of Formula IIa:
Bx is a heterocyclic base moiety;
one of $T_3$ and $T_4$ is an internucleoside linking group attaching the bicyclic nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the bicyclic nucleoside to the remainder of the other of the 5' or 3' end of the oligomeric compound;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each substituted group is, independently, mono or poly substituted with substituent groups independently selected from halogen, $OJ_1$, $SJ_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=O)NJ_1J_2$ and $N(H)C(=S)NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;
n is 1 or 2; and
wherein said oligomeric compound comprises from 8 to 40 monomeric subunits linked by internucleoside linking groups and wherein at least some of the heterocyclic base moieties are capable of hybridizing to a nucleic acid molecule.

In certain embodiments, each Bx is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine. In certain embodiments, each Bx is, independently, a purine, substituted purine, pyrimidine or substituted pyrimidine.

In certain embodiments, at least one 5' or 3'-conjugate group.

In certain embodiments, at least one of $Q_1$, $Q_2$, $G_1$ and $G_2$ is $CH_3$ and the remaining of $Q_1$, $Q_2$, $G_1$ and $G_2$ are each H for each bicyclic nucleoside of Formula IIa. In certain embodiments, $Q_1$, $Q_2$, $G_1$ and $G_2$ are each H for each is bicyclic nucleoside of Formula IIa.

In certain embodiments, n is 1 and the configuration at the sulfur atom is R for each bicyclic nucleoside of Formula IIa. In certain embodiments, n is 1 and the configuration at the sulfur atom is S for each bicyclic nucleoside of Formula IIa. In certain embodiments, n is 2 for each bicyclic nucleoside of Formula IIa.

In certain embodiments, oligomeric compounds are provided comprising from about 8 to about 20 linked monomer subunits.

In certain embodiments, gapped oligomeric compounds are provided comprising a first region consisting of from 2 to 5 modified nucleosides, a second region consisting of from 2 to 5 modified nucleosides and a gap region located between the first and second regions, wherein at least one of the modified nucleosides of the first and second region is a bicyclic nucleoside having Formula IIa and wherein each monomer subunit in the gap region is independently, a nucleoside or a modified nucleoside that is different from each bicyclic nucleoside of Formula IIa and each of the modified nucleosides in the first and second regions.

In certain embodiments, the gap region comprises from about 8 to about 14 contiguous β-D-2'-deoxyribonucleosides.

In certain embodiments, essentially each modified nucleoside of the first and second region is a bicyclic nucleoside having Formula IIa. In certain embodiments, each of the modified nucleosides that is other than a bicyclic nucleoside having Formula II is, independently, a substituted nucleoside having one or more sugar substituent groups, an optionally substituted 4'-S nucleoside or an optionally substituted bicyclic nucleoside.

In certain embodiments, each internucleoside linking group is, independently, a phosphodiester internucleoside linking group or a phosphorothioate internucleoside linking group. In certain embodiments, essentially each internucleoside linking group is a phosphorothioate internucleoside linking group.

In certain embodiments, methods of inhibiting gene expression are provided comprising contacting a cell with an oligomeric compound as provided herein wherein said oligomeric compound is complementary to a target RNA.

In certain embodiments, bicyclic nucleosides are provided herein having Formula I:

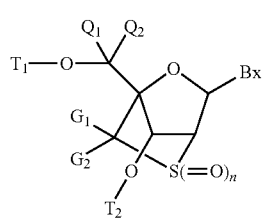

I wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
n is 1 or 2. In certain embodiments, Bx is an optionally protected pyrimidine, substituted pyrimidine, purine or substituted purine. In certain embodiments, Bx is uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine In certain embodiments, $T_1$ is H or a hydroxyl protecting group. In certain embodiments, $T_2$ is a reactive phosphorus group selected from an H-phosphonate or a phosphoramidite. In certain embodiments, $T_1$ is 4,4'-dimethoxytrityl. In certain embodiments, $T_1$ is 4,4'-dimethoxytrityl and $T_2$ is diisopropylcyanoethoxy phosphoramidite.

In certain embodiments, one of $Q_1$ and $Q_2$ is H and the other of $Q_1$ and $Q_2$ is other than H. In certain embodiments, at least one of $Q_1$ and $Q_2$ is $C_1$-$C_6$ alkyl or substituted $C_1$-$C_6$ alkyl. In certain embodiments, at least one of $Q_1$ and $Q_2$ is methyl. In certain embodiments, $Q_1$ and $Q_2$ are each H.

In certain embodiments, one of $G_1$ and $G_2$ is H and the other of $G_1$ and G is other than H. In certain embodiments, at least one of $G_1$ and $G_2$ is $C_1$-$C_6$ alkyl or substituted $C_1$-$C_6$ alkyl. In certain embodiments, at least one of $G_1$ and $G_2$ is methyl. In certain embodiments, $G_1$ and $G_2$ are each H. In certain embodiments, $Q_1$, $Q_2$, $G_1$ and $G_2$ are each H.

In certain embodiments, n is 1. In certain embodiments, n is 2.

In certain embodiments, the bicyclic nucleoside having Formula I has the configuration of Formula Ia:

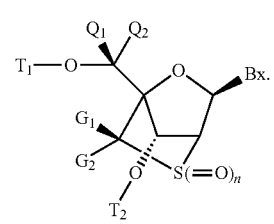

Ia

In certain embodiments, three of $Q_1$, $Q_2$, $G_1$ and $G_2$ are H and the other one of $Q_1$, $Q_2$, $G_1$ and $G_2$ is other than H. In certain embodiments, one of $Q_1$, $Q_2$, $G_1$ and $G_2$ is $CH_3$.

In certain embodiments, n is 1 and the configuration at the sulfur atom is R. In certain embodiments, n is 1 and the configuration at the sulfur atom is S. In certain embodiments, n is 2.

In certain embodiments, oligomeric compounds are provided comprising at least one bicyclic nucleoside of Formula II:

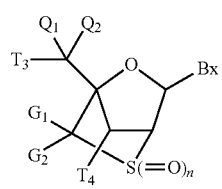

wherein independently for each bicyclic nucleoside of Formula II:

Bx is a heterocyclic base moiety;

one of $T_3$ and $T_4$ is an internucleoside linking group attaching the bicyclic nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the bicyclic nucleoside to the remainder of the other of the 5' or 3' end of the oligomeric compound;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;

n is 1 or 2; and wherein the oligomeric compound comprises from 8 to 40 monomeric subunits linked by internucleoside linking groups and wherein at least some of the heterocyclic base moieties are capable of hybridizing to a nucleic acid molecule.

In certain embodiments, n each Bx is, independently, an optionally protected pyrimidine, substituted pyrimidine, purine or substituted purine. In certain embodiments, each Bx is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine In certain embodiments, at least one of $T_3$ and $T_4$ is a 5' or 3'-terminal group. In certain embodiments, at least one 5' or 3'-terminal group is a conjugate group. In certain embodiments, at least one 5' or 3'-terminal group is a phosphate moiety.

In certain embodiments, one of $Q_1$ and $Q_2$ is H and the other of $Q_1$ and $Q_2$ is other than H for each bicyclic nucleoside of Formula II. In certain embodiments, one of $Q_1$ and $Q_2$ is $C_1$-$C_6$ alkyl or substituted $C_1$-$C_6$ alkyl for each bicyclic nucleoside of Formula II. In certain embodiments, one of $Q_1$ and $Q_2$ is methyl for each bicyclic nucleoside of Formula II. In certain embodiments, one of $Q_1$ and $Q_2$ are each H for each bicyclic nucleoside of Formula II.

In certain embodiments, one of $G_1$ and $G_2$ is H and the other of $G_1$ and $G_2$ is other than H for each bicyclic nucleoside of Formula II. In certain embodiments, one of $G_1$ and $G_2$ is $C_1$-$C_6$ alkyl or substituted $C_1$-$C_6$ alkyl for each bicyclic nucleoside of Formula II. In certain embodiments, one of $G_1$ and $G_2$ is methyl for each bicyclic nucleoside of Formula II. In certain embodiments, $G_1$ and $G_2$ are each H for each bicyclic nucleoside of Formula II. In certain embodiments, $Q_1$, $Q_2$, $G_1$ and $G_2$ are each H for each bicyclic nucleoside of Formula II.

In certain embodiments, n is 1 for each bicyclic nucleoside of Formula II. In certain embodiments, n is 2 for each bicyclic nucleoside of Formula II.

In certain embodiments, oligomeric compounds are provided comprising at least one bicyclic nucleoside of Formula II that each have the configuration of Formula IIa:

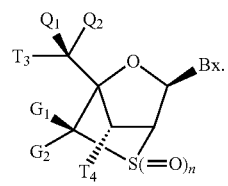

In certain embodiments, three of $Q_1$, $Q_2$, $G_1$ and $G_2$ are H and the other one of $Q_1$, $Q_2$, $G_1$ and $G_2$ is other than H for each bicyclic nucleoside of Formula IIa. In certain embodiments, one of $Q_1$, $Q_2$, $G_1$ and $G_2$ is methyl for each bicyclic nucleoside of Formula IIa. In certain embodiments, $Q_1$, $Q_2$, $G_1$ and $G_2$ are each H for each bicyclic nucleoside of Formula IIa.

In certain embodiments, n is 1 and the configuration at the sulfur atom is R for each bicyclic nucleoside of Formula IIa. In certain embodiments, n is 1 and the configuration at the sulfur atom is S for each bicyclic nucleoside of Formula IIa. In certain embodiments, n is 2 for each bicyclic nucleoside of Formula IIa.

In certain embodiments, oligomeric compounds are provided comprising from about 8 to about 20 linked monomer subunits. In certain embodiments, oligomeric compounds are provided comprising from about 10 to about 18 linked monomer subunits. In certain embodiments, oligomeric compounds are provided comprising from about 12 to about 16 linked monomer subunits.

In certain embodiments, oligomeric compounds are provided comprising a first region consisting of from 2 to 5 modified nucleosides, wherein at least one of the modified nucleosides of the first region is a bicyclic nucleoside having Formula II. In certain embodiments, oligomeric compounds are provided comprising a first region consisting of from 2 to 5 modified nucleosides and a second region consisting of from two to 5 modified nucleosides wherein at least one of the modified nucleosides of the first region is a bicyclic nucleoside having Formula II. In certain embodiments, oligomeric compounds are provided comprising a first region consisting of from 2 to 5 modified nucleosides and a second region consisting of from two to 5 modified nucleosides wherein at least one of the modified nucleosides of the first region is a bicyclic nucleoside having Formula II and at least one of the modified nucleosides of the second region is a bicyclic nucleoside having Formula II.

In certain embodiments, oligomeric compounds are provided comprising a gap region located between the first and second regions wherein each monomer subunit in the gap region is independently, a nucleoside or a modified nucleoside that is different from each bicyclic nucleoside of Formula II and each of the modified nucleosides in the first and second regions. In certain embodiments, the gap region comprises from about 6 to about 14 monomer subunits. In certain embodiments, the gap region comprises from about 8 to about 14 contiguous β-D-2'-deoxyribonucleosides. In certain embodiments, the gap region comprises from about 9 to about 12 contiguous β-D-2'-deoxyribonucleosides. In certain embodiments, essentially each modified nucleoside of the first region is a bicyclic nucleoside having Formula II. In certain embodiments, essentially each modified nucleoside of the first and second regions is a bicyclic nucleoside having Formula II.

In certain embodiments, oligomeric compounds are provided wherein each of the modified nucleosides that is other than a bicyclic nucleoside having Formula II is, independently, a substituted nucleoside having one or more sugar substituent groups, an optionally substituted 4'-S nucleoside or an optionally substituted bicyclic nucleoside. In certain embodiments, each of the modified nucleosides that is other than a bicyclic nucleoside having Formula II is, independently, a 2' substituted nucleoside comprising a 2'-fluoro, 2'-O—$CH_3$, 2'-O—$(CH_2)_2$—O—$CH_3$ or 2'-O—$CH_2C$(=O)—N(H)($CH_3$) sugar substituent group. In certain embodiments, each of the modified nucleosides that is other than a bicyclic nucleoside having Formula II is a 2' substituted nucleoside comprising a 2'-O—$(CH_2)_2$—O—$CH_3$ sugar substituent group.

In certain embodiments, oligomeric compounds are provided wherein each bicyclic nucleoside of Formula II has the configuration of Formula IIa.

In certain embodiments, oligomeric compounds are provided wherein each internucleoside linking group is, independently, a phosphodiester internucleoside linking group or a phosphorothioate internucleoside linking group. In certain embodiments, essentially each internucleoside linking group is a phosphorothioate internucleoside linking group.

In certain embodiments, methods of inhibiting gene expression are provided comprising contacting a cell with an oligomeric compound of any of the claims wherein the oligomeric compound is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the methods further comprise detecting the levels of target RNA.

In certain embodiments, methods of inhibiting gene expression are provided comprising contacting one or more cells or a tissue with an oligomeric compound of any of the claims.

In certain embodiments, oligomeric compounds are provided for therapeutic use in an in vivo method of inhibiting gene expression the method comprising contacting an animal with an oligomeric compound as provided herein.

In certain embodiments, oligomeric compounds are provided for use in medical therapy.

DETAILED DESCRIPTION OF THE INVENTION

Provided herein are novel substituted 2'-thio bicyclic nucleosides and oligomeric compounds prepared therefrom. More particularly, the substituted 2'-thio bicyclic nucleosides provided herein include a furanose ring system having a bridge comprising an optionally substituted 4'-methylene group attached to a 2'-sulfoxide or sulfone group and optionally include one or more substituent groups attached to the 5'-position. In certain embodiments, the oligomeric compounds provided herein are expected to hybridize to a portion of a target RNA resulting in loss of normal function of the target RNA.

Incorporation of one or more of the substituted 2'-thio bicyclic nucleosides, as provided herein, into an oligomeric compound is expected to enhance one or more desired properties of the resulting oligomeric compound. Such properties include without limitation stability, nuclease resistance, binding affinity, specificity, absorption, cellular distribution, cellular uptake, charge, pharmacodynamics and pharmacokinetics.

In certain embodiments, the substituted 2'-thio bicyclic nucleosides provided herein are incorporated into antisense oligomeric compounds which are used to reduce target RNA, such as messenger RNA, in vitro and in vivo. The reduction of target RNA can be effected via numerous pathways with a resultant modulation of gene expression. Such modulation can provide direct or indirect increase or decrease in a particular target (nucleic acid or protein). Such pathways include for example the steric blocking of transcription or translation and cleavage of mRNA using either single or double stranded oligomeric compounds. The oligomeric compounds provided herein are also expected to be useful as primers and probes in diagnostic applications. In certain embodiments, oligomeric compounds comprising at least one of the substituted 2'-thio bicyclic nucleosides provided herein are expected to be useful as aptamers which are oligomeric compounds capable of binding to aberrant proteins in an in vivo setting.

In certain embodiments, the substituted 2'-thio bicyclic nucleosides provided herein each have Formula I:

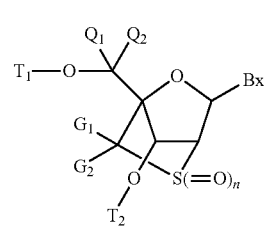

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and n is 1 or 2.

In certain embodiments, each of the substituted 2'-thio bicyclic nucleosides having Formula I further have the configuration of Formula Ia:

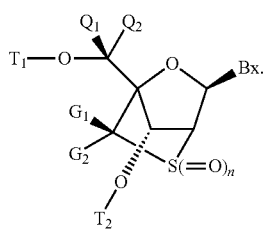

Ia

In certain embodiments, oligomeric compounds are provided comprising at least one bicyclic nucleoside of Formula II:

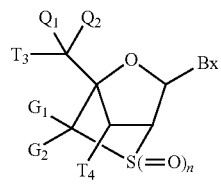

II wherein independently for each bicyclic nucleoside of Formula II:

Bx is a heterocyclic base moiety;

one of $T_3$ and $T_4$ is an internucleoside linking group attaching the bicyclic nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the bicyclic nucleoside to the remainder of the other of the 5' or 3' end of the oligomeric compound;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;

n is 1 or 2; and wherein said oligomeric compound comprises from 8 to 40 monomeric subunits linked by internucleoside linking groups and wherein at least some of the heterocyclic base moieties are capable of hybridizing to a nucleic acid molecule.

In certain embodiments, oligomeric compounds are provided comprising at least one bicyclic nucleoside of Formula II wherein each bicyclic nucleoside of Formula II further has the configuration of Formula IIa:

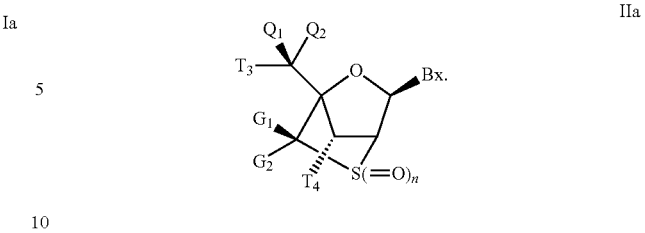

IIa

In certain embodiments, the substituted 2'-thio bicyclic nucleosides provided herein are incorporated into oligomeric compounds such that a motif results. The placement of substituted 2'-thio bicyclic nucleosides into oligomeric compounds to provide particular motifs can enhance the desired properties of the resulting oligomeric compounds for activity using various mechanisms such as for example RNaseH or RNAi. Such motifs include without limitation, gapmer motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include terminal groups at one or both of the 5' and or 3' terminals such as a conjugate or reporter group. The positioning of the substituted 2'-thio bicyclic nucleosides provided herein, the use of linkage strategies and terminal groups can be easily optimized to enhance a desired activity for a selected target.

As used herein the term "motif" refers to the pattern created by the relative positioning of monomer subunits within an oligomeric compound wherein the pattern is determined by comparing the sugar moieties of the linked monomer subunits. The only determinant for the motif of an oligomeric compound is the differences or lack of differences between the sugar moieties. The internucleoside linkages, heterocyclic bases and further groups such as terminal groups are not considered when determining the motif of an oligomeric compound.

The preparation of motifs has been disclosed in various publications including without limitation, representative U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922; and published international applications WO 2005/121371 and WO 2005/121372 (both published on Dec. 22, 2005), certain of which are commonly owned with the instant application, and each of which is herein incorporated by reference in its entirety.

As used herein the term "alternating motif" refers to an oligomeric compound comprising a contiguous sequence of linked monomer subunits wherein the monomer subunits have two different types of sugar moieties that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar moieties, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' and or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, each A or each B comprise 2'-thio bicyclic nucleosides as provided herein.

As used herein the term "uniformly fully modified motif" refers to an oligomeric compound comprising a contiguous sequence of linked monomer subunits that each have the same type of sugar moiety. The heterocyclic base and internucleoside linkage is independently variable at each position. The motif further optionally includes the use of one or more other groups including but not limited to capping groups, conjugate groups and other 5' and or 3'-terminal groups. In certain embodiments, the uniformly fully modified motif includes a contiguous sequence of 2'-thio bicyclic nucleosides. In certain embodiments, one or both of the 5' and 3'-ends of the contiguous sequence of 2'-thio bicyclic nucleosides, comprise 5' and or 3'-terminal groups such as one or more unmodified nucleosides.

As used herein the term "hemimer motif" refers to an oligomeric compound comprising a contiguous sequence of monomer subunits that each have the same type of sugar moiety with a further short contiguous sequence of monomer subunits located at the 5' or the 3' end that have a different type of sugar moiety. The heterocyclic base and internucleoside linkage is independently variable at each position. The motif further optionally includes the use of one or more other groups including but not limited to capping groups, conjugate groups and other 5' and or 3'-terminal groups. In general, a hemimer is an oligomeric compound of uniform sugar moieties further comprising a short region (1, 2, 3, 4 or about 5 monomer subunits) having uniform but different sugar moieties located on either the 3' or the 5' end of the oligomeric compound.

In certain embodiments, the hemimer motif comprises a contiguous sequence of from about 10 to about 28 monomer subunits having one type of sugar moiety with from 1 to 5 or from 2 to about 5 monomer subunits having a second type of sugar moiety located at one of the termini. In certain embodiments, the hemimer is a contiguous sequence of from about 8 to about 20 β-D-2'-deoxyribonucleosides having from 1-12 contiguous 2'-thio bicyclic nucleosides located at one of the termini. In certain embodiments, the hemimer is a contiguous sequence of from about 8 to about 20 β-D-2'-deoxyribonucleosides having from 1-5 contiguous 2'-thio bicyclic nucleosides located at one of the termini. In certain embodiments, the hemimer is a contiguous sequence of from about 12 to about 18 β-D-2'-deoxyribonucleosides having from 1-3 contiguous 2'-thio bicyclic nucleosides located at one of the termini. In certain embodiments, the hemimer is a contiguous sequence of from about 10 to about 14 β-D-2'-deoxyribonucleosides having from 1-3 contiguous 2'-thio bicyclic nucleosides located at one of the termini.

As used herein the terms "blockmer motif" and "blockmer" refer to an oligomeric compound comprising an otherwise contiguous sequence of monomer subunits wherein the sugar moieties of each monomer subunit is the same except for an interrupting internal block of contiguous monomer subunits having a different type of sugar moiety. The heterocyclic base and internucleoside linkage is independently variable at each position of a blockmer. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar moieties in a blockmer and only the monomer subunits in the external regions have non-naturally occurring sugar moieties in a gapmer with the remainder of monomer subunits in the blockmer or gapmer being β-D-2'-deoxyribonucleosides or β-D-ribonucleosides. In certain embodiments, blockmers are provided herein wherein all of the monomer subunits comprise non-naturally occurring sugar moieties.

As used herein the term "positionally modified motif" is meant to include an otherwise contiguous sequence of monomer subunits having one type of sugar moiety that is interrupted with two or more regions of from 1 to about 5 contiguous monomer subunits having another type of sugar moiety. Each of the two or more regions of from 1 to about 5 contiguous monomer subunits are independently uniformly modified with respect to the type of sugar moiety. In certain embodiments, each of the two or more regions have the same type of sugar moiety. In certain embodiments, each of the two or more regions have a different type of sugar moiety. In certain embodiments, each of the two or more regions, independently, have the same or a different type of sugar moiety. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of from 2 to about 5 contiguous 2'-thio bicyclic nucleosides each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar moieties of the external regions being different than the sugar moieties of the internal region and wherein the sugar moiety of each monomer subunit within a particular region is essentially the same. In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar moieties with the internal region comprising β-D-2'-deoxyribonucleosides. In certain embodiments, the external regions each, independently, comprise from 1 to about 5 monomer subunits having non-naturally occurring sugar moieties and the internal region comprises from 6 to 18 unmodified nucleosides. The internal region or the gap generally comprises β-D-2'-deoxyribonucleosides but can comprise non-naturally occurring sugar moieties. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising 2'-thio bicyclic nucleosides as disclosed herein. In certain embodiments, the gapped oligomeric compounds comprise an internal region of β-D-2'-deoxyribonucleosides with one of the external regions comprising 2'-thio bicyclic nucleosides as disclosed herein and the other external region comprising modified nucleosides different than the 2'-thio bicyclic nucleosides as disclosed herein. In certain embodiments, the gapped oligomeric compounds comprise an internal region of β-D-2'-deoxyribonucleosides with both of the external regions comprising 2'-thio bicyclic nucleosides as provided herein. In certain embodiments, the gapped oligomeric compounds comprise an internal region of β-D-2'-deoxyribonucleosides with both of the external regions comprising a mixture of 2'-thio bicyclic nucleosides as provided herein and at least one other modified nucleosides different from the 2'-thio bicyclic nucleosides as provided herein. In certain embodiments, gapped oligomeric compounds are provided herein wherein all of the monomer subunits comprise non-naturally occurring sugar moieties.

In certain embodiments, gapped oligomeric compounds are provided comprising one or two 2'-thio bicyclic nucleosides at the 5'-end, two or three 2'-thio bicyclic nucleosides at the 3'-end and an internal region of from 10 to 16 β-D-2'-deoxyribonucleosides. In certain embodiments, gapped oligomeric compounds are provided comprising one of the 2'-thio bicyclic nucleosides at the 5'-end, two 2'-thio bicyclic nucleosides at the 3'-end and an internal region of from 10 to 16 β-D-2'-deoxyribonucleosides. In certain embodiments, gapped oligomeric compounds are provided comprising one 2'-thio bicyclic nucleosides at the 5'-end, two 2'-thio bicyclic nucleosides at the 3'-end and an internal region of from 10 to 14 β-D-2'-deoxyribonucleosides. In certain embodiments, gapped oligomeric compounds are provided comprising one or more 2'-thio bicyclic nucleosides at the 5'-end, one or more 2'-thio bicyclic nucleosides at the 3'-end and an internal region of from 8 to 14 β-D-2'-deoxyribonucleosides wherein each of the 3'-end and 5'-end further include from 1 to 3 modified nucleosides different from the 2'-thio bicyclic nucleosides. In certain embodiments, gapped oligomeric compounds are provided comprising one or more 2'-thio bicyclic nucleosides at the 5'-end, one or more 2'-thio bicyclic nucleosides at the 3'-end and an internal region of from 8 to 14 β-D-2'-deoxyribonucleosides wherein each of the 3'-end and 5'-end further include from 1 to 3 MOE modified nucleosides.

In certain embodiments, gapped oligomeric compounds are provided that are from about 18 to about 21 monomer subunits in length. In certain embodiments, gapped oligomeric compounds are provided that are from about 16 to about 21 monomer subunits in length. In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length. In certain embodiments, gapped oligomeric compounds are provided that are from about 14 to about 16 monomer subunits in length.

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "aralkyl" and "arylalkyl," refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethylene, pyrimidinylethylene, napthyridinylpropylene and the like. Heteroarylalkyl groups as used herein may optionally include further substituent groups on one or both of the heteroaryl or alkyl portions.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more additional heteroatoms selected from N and S and can be further mono or poly substituted with one or more substituent groups.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein the terms "halo" and "halogen," refer to an atom selected from fluorine, chlorine, bromine and iodine.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.,* 1977, 99, 7363-7365; Barany et al., *J. Am. Chem. Soc.,* 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

The terms "substituent" and "substituent group," as used herein, are meant to include groups that are typically added to a parent compounds or to further substituted substituent groups to enhance one or more desired properties or provide other desired effects. Substituent groups can be protected or unprotected and can be added to one available site or many available sites on a parent compound. As an example if a benzene is substituted with a substituted alky it will not have any overlap with a benzene that is substituted with substituted hydroxyl. In such an example the alkyl portion of the substituted alkyl is covalently linked by one of its carbon atoms to one of the benzene carbon atoms. If the alky is $C_1$ and it is substituted with a hydroxyl substituent group (substituted alkyl) then the resultant compound is benzyl alcohol ($C_6H_5CH_2OH$). If the benzene were substituted with a substituted hydroxyl group and the hydroxyl was substituted with a $C_1$ alkyl group then the resultant compound would be anisole ($C_6H_5OCH_3$).

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—N$_3$), nitro (—NO$_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein the term "nucleobase" generally refers to the nucleobase of a nucleoside or modified nucleoside. The term "heterocyclic base moiety" is broader than the term nucleobase in that it includes any heterocyclic base that can be attached to a sugar to prepare a nucleoside or modified nucleoside. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines).

In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. In certain embodiments, nucleobase refers to unmodified or naturally occurring nucleobases which include, but are not limited to, the purine bases adenine (A) and guanine (G), and the pyrimidine bases thymine (T), cytosine (C) and uracil (U) and analogs thereof such as 5-methyl cytosine. The terms nucleobase and heterocyclic base moiety also include optional protection for any reactive functional groups such as 4-N-benzoylcytosine, 4-N-benzoyl-5-methylcytosine, 6-N-benzoyladenine or 2-N-isobutyrylguanine In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302). Modified polycyclic heterocyclic compounds useful as heterocyclic base moieties are disclosed in the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

As used herein the term "sugar moiety" refers to naturally occurring sugars having a furanose ring system (ribose and 2'-deoxyribose), synthetic and/or non-naturally occurring sugars having a modified furanose ring system and sugar surrogates wherein the furanose ring has been replaced with a mono or polycyclic ring system such as for example a morpholino or hexitol ring system or a non-cyclic sugar surrogate such as that used in peptide nucleic acids. The sugar moiety of a monomer subunit provides the reactive groups that enable the linking of adjacent monomer subunits into an oligomeric compound. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose wherein the ring oxygen atom has been replaced with a sulfur atom), bicyclic modified sugars (such as the 2'-O—CH(CH$_3$)-4',2'-O—CH$_2$-4' or 2'-O—(CH$_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

As used herein the term "sugar substituent group" refers to a group that is covalently attached to a sugar moiety. In certain embodiments, examples of sugar substituent groups include without limitation halogen, alkyl, substituted alkyl, alkoxy, substituted alkoxy, alkenyl, substituted alkenyl, alkynyl, substituted alkynyl, amino, substituted amino, thio, substituted thio and azido. In certain embodiments the alkyl and alkoxy groups are $C_1$ to $C_6$. In certain embodiments, the alkenyl and alkynyl groups are $C_2$ to $C_6$. In certain embodiments, examples of sugar substituent groups include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-OCH$_3$, 2'-O(CH$_2$)$_n$CH$_3$, 2'-OCH$_2$CH$_3$, 2'-O—(CH$_2$)$_2$CH$_3$, 2'-O—(CH$_2$)$_2$—O—CH$_3$ (MOE), 2'—O[(CH$_2$)$_n$O]$_m$CH$_3$, 2'-O(CH$_2$)$_2$SCH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)$_n$ON[(CH$_2$)$_n$CH$_3$]$_2$, 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], wherein each R$_p$, R$_q$ and R$_r$ is, independently, H, substituted or unsubstituted C$_1$-C$_{10}$ alkyl or a protecting group and where n and m are from 1 to about 10.

In certain embodiments, examples of sugar substituent groups include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-O—CH$_3$, OCF$_3$, 2'-O—CH$_2$CH$_3$, 2'-O—(CH$_2$)$_2$CH$_3$, 2'-O—(CH$_2$)$_2$—O—CH$_3$ (MOE), 2'-O(CH$_2$)$_2$SCH$_3$, 2'-O—CH$_2$—CH=CH$_2$, 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$)[N(R$_m$)(R$_n$)] wherein each R$_m$ and R$_n$ is, independently, H, substituted or unsubstituted C$_1$-C$_{10}$ alkyl or a protecting group. In certain embodiments, examples of 2,-sugar substituent groups include without limitation fluoro, —O—CH$_3$, —O—CH$_2$CH$_3$, —O—(CH$_2$)$_2$CH$_3$, —O—(CH$_2$)$_2$—O—CH$_3$, —O—CH$_2$—CH=CH$_2$, —O—(CH$_2$)$_3$—N(R$_1$)(R$_2$), O—(CH$_2$)$_2$—O—N(R$_1$)(R$_2$), —O—(CH$_2$)$_2$—O—(CH$_2$)$_2$—N(R$_1$)(R$_2$), —O—CH$_2$C(=O)—N(R$_1$)(R$_2$), —O—CH$_2$C(=O)—N(H)—(CH$_2$)$_2$—N(R$_1$)(R$_2$) and —O—CH$_2$—N(H)—C(=NR$_1$)[N(R$_1$)(R$_2$)] wherein R$_1$ and R$_2$ are each independently, H or C$_1$-C$_2$ alkyl. In certain embodiments, examples of sugar substituent groups include without limitation fluoro, —O—CH$_3$, —O—(CH$_2$)$_2$—O—

$CH_3$, —O—$CH_2$C(=O)—N(H)($CH_3$), —O—$CH_2$C(=O)—N(H)—($CH_2$)$_2$—N($CH_3$)$_2$ and —O—$CH_2$—N(H)—C(=N$CH_3$)[N($CH_3$)$_2$]. In certain embodiments, examples of sugar substituent groups include without limitation fluoro, —O—$CH_3$, —O—($CH_2$)$_2$—O—$CH_3$, —O—$CH_2$C(=O)—N(H)($CH_3$) and —O—$CH_2$C(=O)—N(H)—($CH_2$)$_2$—N($CH_3$)$_2$. Further examples of modified sugar moieties include without limitation bicyclic sugars (e.g. bicyclic nucleic acids or bicyclic nucleosides discussed below).

In certain embodiments, sugar substituent groups include without limitation one or two 5'-sugar substituent groups independently selected from $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and halogen. In certain embodiments, examples of sugar substituent groups include without limitation one or two 5'-sugar substituent groups independently selected from vinyl, 5'-methyl, 5'-(S)-methyl and 5'-(R)-methyl. In certain embodiments, examples of sugar substituent groups include without limitation one 5'-sugar substituent group selected from vinyl, 5'-(S)-methyl and 5'-(R)-methyl.

In certain embodiments, examples of sugar substituent groups include without limitation substituted silyl, an RNA cleaving group, a reporter group, an intercalator, a group for improving pharmacokinetic properties, or a group for improving the pharmacodynamic properties of an oligomeric compound, and other substituents having similar properties. In certain embodiments, oligomeric compounds include modified nucleosides comprising 2'-MOE substituent groups (Baker et al., J. Biol. Chem., 1997, 272, 11944-12000). Such 2'-MOE substitution has been described as having improved binding affinity compared to unmodified nucleosides and to other modified nucleosides, such as 2'-O-methyl, 2'-O-propyl, and 2'-O-aminopropyl. Oligonucleotides having the 2'-MOE substituent also have been shown to be antisense inhibitors of gene expression with promising features for in vivo use (Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

Sugar moieties can be substituted with more than one sugar substituent group including without limitation 2'-F-5'-methyl substituted nucleosides (see PCT International Application WO 2008/101157, published on Aug. 21, 2008 for other disclosed 5',2'-bis substituted nucleosides). Other combinations are also possible, including without limitation, replacement of the ribosyl ring oxygen atom with S and further substitution at the 2'-position (see published U.S. Patent Application US2005-0130923, published on Jun. 16, 2005) and 5'-substitution of a bicyclic nucleoside (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group).

As used herein the term "monomer subunit" is meant to include all manner of monomers that are amenable to oligomer synthesis. In general a monomer subunit includes at least a sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribonucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides and nucleosides having sugar surrogates. As used herein, the term "nucleoside" refers to a nucleobase-sugar combination. The two most common classes of such nucleobases are purines and pyrimidines. The term nucleoside includes β-D-ribonucleosides and β-D-2'-deoxyribonucleosides.

As used herein, the term "nucleotide" refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose ring system or a modified furanose ring system. Modified furanose ring systems include 4'-S analogs, one or more substitutions at any position such as for example the 2', 3', 4' and 5' positions and addition of bridges for form additional rings such as a 2'-O—CH($CH_3$)-4' bridge. Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-5-2'-substituted ribonucleosides), bicyclic modified nucleosides (such as 2'-O—CH($CH_3$)-4',2'-O—$CH_2$-4' or 2'-O—($CH_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons atoms. In certain embodiments, bicyclic nucleosides have a bridge between the 4' and 2' carbon atoms. Examples of such 4' to 2' bridged bicyclic nucleosides, include but are not limited to one of formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-C—H (CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N (OCH$_3$)-2' (and analogs thereof see published International Application WO2008/150729, published Dec. 11, 2008); 4'-CH$_2$—O—N(CH$_3$)-2' (see U.S. Pat. No. 7,696,345, issued on Apr. 13, 2010,); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., J. Org. Chem., 2009, 74, 118-134); and 4'-CH$_2$—CH$_2$-2' and 4'-CH$_2$—C—(=CH$_2$)-2' (and analogs thereof see published International Application WO 2008/154401, published on Dec. 8, 2008). Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A., 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,741,457; 7,696,345; 7,547,684,;7,399,845; 7,053,207; 7,034,133; 6,794,499; 6,770,748; 6,670,461; 6,525,191; 6,268,490; U.S. Patent Publication Nos.: US2008-0039618; U.S. Patent Applications, Ser. Nos. 61/099,844; 61/097,787; 61/086,231; 61/056,564; 61/026,998; 61/026,995; 60/989,574; International applications WO2009/006478; WO2008/154401; WO2008/150729; WO 2007/134181; WO 2005/021570; WO 2004/106356; WO 94/14226). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups (generally forming a 4 to 6 membered ring with the parent sugar moiety) independently selected from —[C(R$_a$)(R$_b$)]$_n$—, —C(R$_a$)=C (R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl(S(=O)$_2$-J$_1$), or sulfoxyl(S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl(C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy(4'-CH$_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2',4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiments, bicyclic nucleosides have the formula:

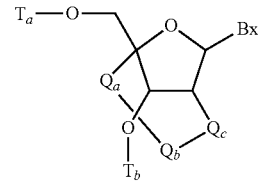

wherein:

Bx is a heterocyclic base moiety;

-Q$_a$-Q$_b$-Q$_c$- is —CH$_2$—N(R$_c$)—CH$_2$—, —C(=O)—N (R$_c$)—CH$_2$—, —CH$_2$—O—N(R$_c$)—, —CH$_2$—N(R$_c$)—O— or —N(R$_c$)—O—CH$_2$;

R$_c$ is C$_1$-C$_{12}$ alkyl or an amino protecting group; and

T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides have the formula:

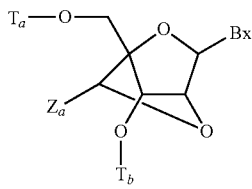

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

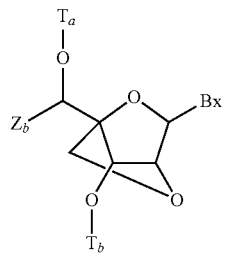

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl(C(=O)—).

In certain embodiments, bicyclic nucleosides have the formula:

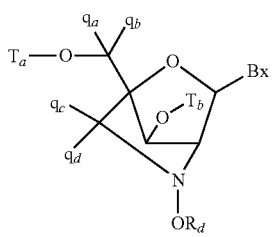

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

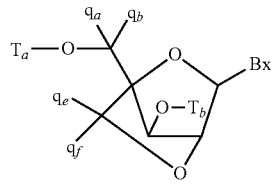

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-CH$_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-CH$_2$—O-2' and 4'-CH$_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

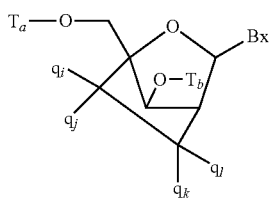

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy(4'-CH$_2$—O-2') BNA, (B) β-D-methyleneoxy(4'-CH$_2$—O-2) BNA (C) ethyleneoxy(4'-(CH$_2$)$_2$—O-2') BNA (D) aminooxy(4'-CH$_2$—O—N(R)-2') BNA, (E) oxyamino(4'-CH$_2$—N(R)—O-2') BNA, (F) methyl(methyleneoxy) (4'-CH(CH$_3$)—O-2) BNA (also referred to as constrained ethyl or cEt), (G) methylene-thio (4'-CH$_2$—S-2') BNA, (H) methylene-amino(4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

(A)

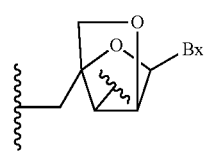

(B)

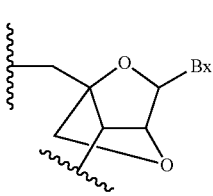

(C)

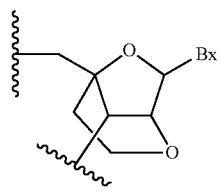

(D)

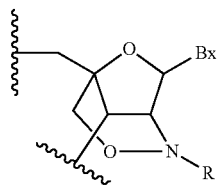

(E)

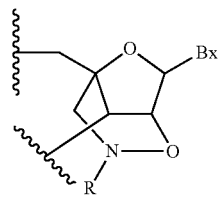

(F)

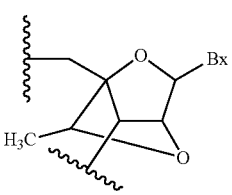

(G)

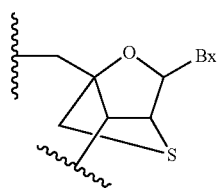

(H)

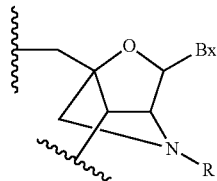

(I)

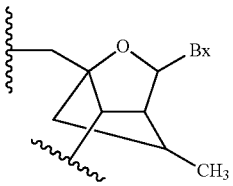

(J)

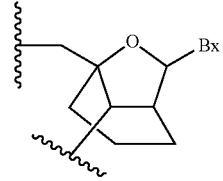

-continued

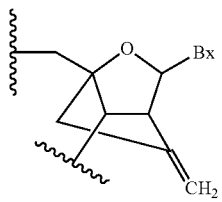
(K)

wherein Bx is the base moiety and R is, independently, H, a protecting group, $C_1$-$C_6$ alkyl or $C_1$-$C_6$ alkoxy.

In certain embodiments, modified nucleosides include nucleosides having sugar surrogate groups that include without limitation, replacement of the ribosyl ring with a sugar surrogate such as a tetrahydropyranyl ring system (also referred to as hexitol) as illustrated below:

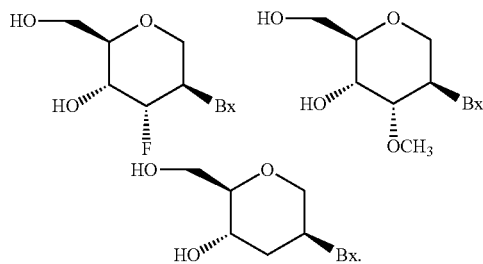

In certain embodiments, sugar surrogates are selected having the formula:

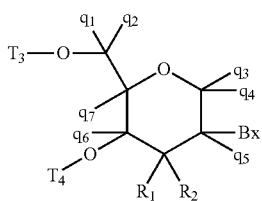

wherein:

Bx is a heterocyclic base moiety;

one of $T_3$ and $T_4$ is an internucleoside linking group attaching the tetrahydropyran nucleoside analog to the remainder of one of the 5' or 3' end of the oligomeric compound and the other of $T_3$ and $T_4$ is hydroxyl, a protected hydroxyl, a 5' or 3' terminal group or an internucleoside linking group attaching the tetrahydropyran nucleoside analog to the remainder of the other of the 5' or 3' end of the oligomeric compound;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F.

In certain embodiments, $R_1$ is fluoro and $R_2$ is H; $R_1$ is methoxy and $R_2$ is H, and $R_1$ is methoxyethoxy and $R_2$ is H.

Such sugar surrogates can be referred to as a "modified tetrahydropyran nucleoside" or "modified THP nucleoside". Modified THP nucleosides include, but are not limited to, what is referred to in the art as hexitol nucleic acid (HNA), altritol nucleic acid (ANA), and mannitol nucleic acid (MNA) (see Leumann, C. J., *Bioorg. & Med. Chem.*, 2002, 10, 841-854).

In certain embodiments, oligomeric compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horváth et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

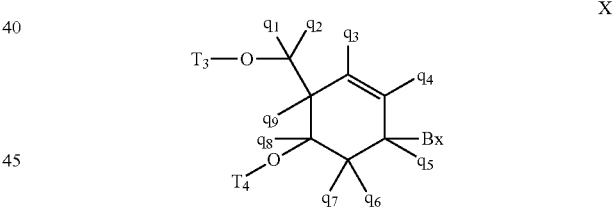
X wherein independently for each of said at least one cyclohexenyl nucleoside analog of Formula X:

Bx is a heterocyclic base moiety;

one of $T_3$ and $T_4$ is an internucleoside linking group attaching the cyclohexenyl nucleoside analog to the remainder of one of the 5' or 3' end of the oligomeric compound and the other of $T_3$ and $T_4$ is hydroxyl, a protected hydroxyl, a 5' or 3' terminal group or an internucleoside linking group attaching the cyclohexenyl nucleoside analog to the remainder of the other of the 5' or 3' end of the oligomeric compound; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

The 2'-thio bicyclic nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry*, in 9 Volumes, Barry M. Trost, Editor-in-Chief, Pergamon Press, New York, 1993; *Advanced Organic Chemistry, Part B: Reactions and Synthesis*, 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis*, 4th Edition, John Wiley & Sons, New York, 1991; and Larock, R. C., *Comprehensive Organic Transformations*, 2nd Edition, John Wiley & Sons, New York, 1999.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in $P^{III}$ or $P^{V}$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite ($-O^*-P[N[(CH(CH_3)_2]_2]O(CH_2)_2CN$) and H-phosphonate ($-O^*-P(=O)(H)OH$), wherein the O* is normally attached to the 3'-position of the Markush group of Formula II or IIa. A preferred synthetic solid phase synthesis utilizes phosphoramidites ($P^{III}$ chemistry) as reactive phosphites. The intermediate phosphite compounds are subsequently oxidized to the phosphate or thiophosphate ($P^{V}$ chemistry) using known methods to yield, phosphodiester or phosphorothioate internucleoside linkages. Chiral auxiliaries are known in the art (see for example: Wang et al., *Tetrahedron Letters*, 1997, 38(5), 705-708; Jin et al., *J. Org. Chem.*, 1997, 63, 3647-3654; Wang et al., *Tetrahedron Letters*, 1997, 38(22), 3797-3800; and U.S. Pat. No. 6,867,294, issued Mar. 15, 2005). Additional reactive phosphates and phosphites are disclosed in Tetrahedron Report Number 309 (Beaucage and Iyer, *Tetrahedron*, 1992, 48, 2223-2311).

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and $CH_2$ component parts.

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

When preparing oligomeric compounds having specific motifs as disclosed herein it can be advantageous to mix non-naturally occurring monomer subunits such as the 2'-thio bicyclic nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits wherein at least one monomer subunit is a 2'-thio bicyclic nucleoside as provided herein. In certain embodiments, oligomeric compounds are provided comprising a plurality of 2'-thio bicyclic nucleosides as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and/or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids. In certain embodiments, antisense activity is assessed by observing a phenotypic change in a cell or animal.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are non-ionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

As used herein the terms "linking groups" and "bifunctional linking moieties" are meant to include groups known in the art that are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

As used herein the term "phosphate moiety" refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

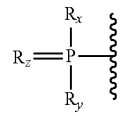

wherein:
$R_x$ and $R_y$ are each, independently, hydroxyl, protected hydroxyl group, thiol, protected thiol group, $C_1$-$C_6$ alkyl, substituted $C_1$-$C_6$ alkyl, $C_1$-$C_6$ alkoxy, substituted $C_1$-$C_6$ alkoxy, a protected amino or substituted amino; and
$R_z$ is O or S.

As a monomer such as a phosphoramidite or H-phosphonate the protected phosphorus moiety is preferred to maintain stability during oligomer synthesis. After incorporation into an oligomeric compound the phosphorus moiety can include deprotected groups.

Phosphorus moieties included herein can be attached to a monomer, which can be used in the preparation of oligomeric compounds, wherein the monomer may be attached using O, S, $NR_d$ or $CR_eR_f$, wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

RNA duplexes exist in what has been termed "A Form" geometry while DNA duplexes exist in "B Form" geometry. In general, RNA:RNA duplexes are more stable, or have higher melting temperatures ($T_m$) than DNA:DNA duplexes (Sanger et al., *Principles of Nucleic Acid Structure,* 1984, Springer-Verlag; New York, N.Y.; Lesnik et al., *Biochemistry,* 1995, 34, 10807-10815; Conte et al., *Nucleic Acids Res.,* 1997, 25, 2627-2634). The increased stability of RNA has been attributed to several structural features, most notably the improved base stacking interactions that result from an A-form geometry (Searle et al., *Nucleic Acids Res.,* 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., *Biochemistry,* 1996, 35, 8489-8494). On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure,* Springer-Verlag, New York, N.Y.).

The relative ability of a chemically-modified oligomeric compound to bind to complementary nucleic acid strands, as compared to natural oligonucleotides, is measured by obtaining the melting temperature of a hybridization complex of said chemically-modified oligomeric compound with its complementary unmodified target nucleic acid. The melting temperature ($T_m$), a characteristic physical property of double helixes, denotes the temperature in degrees centigrade at which 50% helical versus coiled (unhybridized) forms are present. $T_m$ (also commonly referred to as binding affinity) is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$.

It is known in the art that the relative duplex stability of an antisense compound:RNA target duplex can be modulated through incorporation of chemically-modified nucleosides into the antisense compound. Sugar-modified nucleosides have provided the most efficient means of modulating the $T_m$ of an antisense compound with its target RNA. Sugar-modified nucleosides that increase the population of or lock the sugar in the C3'-endo (Northern, RNA-like sugar pucker) configuration have predominantly provided a per modification $T_m$ increase for antisense compounds toward a complementary RNA target. Sugar-modified nucleosides that increase the population of or lock the sugar in the C2'-endo (Southern, DNA-like sugar pucker) configuration predominantly provide a per modification Tm decrease for antisense compounds toward a complementary RNA target. The sugar pucker of a given sugar-modified nucleoside is not the only factor that dictates the ability of the nucleoside to increase or decrease an antisense compound's $T_m$ toward complementary RNA. For example, the sugar-modified nucleoside tricycloDNA is predominantly in the C2'-endo conformation, however it imparts a 1.9 to 3° C. per modification increase in $T_m$ toward a complementary RNA. Another example of a sugar-modified high-affinity nucleoside that does not adopt the C3'-endo conformation is α-L-LNA (described in more detail herein).

As used herein, "$T_m$" means melting temperature which is the temperature at which the two strands of a duplex nucleic acid separate. $T_m$ is often used as a measure of duplex stability or the binding affinity of an antisense compound toward a complementary strand such as an RNA molecule.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases or more broadly, heterocyclic base moieties, comprising certain modifications may maintain the ability to pair with a counterpart nucleobase and thus, are still capable of complementarity.

As used herein, "non-complementary" "in reference to nucleobases refers to a pair of nucleobases that do not form hydrogen bonds with one another or otherwise support hybridization.

As used herein, "complementary" in reference to linked nucleosides, oligonucleotides, oligomeric compounds, or nucleic acids, refers to the capacity of an oligomeric compound to hybridize to another oligomeric compound or nucleic acid through nucleobase or more broadly, heterocyclic base, complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an antisense compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, the term "pharmaceutically acceptable salts" refers to salts that retain the desired activity of the compound and do not impart undesired toxicological effects thereto. The term "pharmaceutically acceptable salt" includes a salt prepared from pharmaceutically acceptable non-toxic acids or bases, including inorganic or organic acids and bases.

Pharmaceutically acceptable salts of the oligomeric compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the oligomeric compounds described herein are in the form of a sodium salt.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include 5' and/or 3'-terminal groups including but not limited to protecting groups such as hydroxyl protecting groups, optionally linked conjugate groups and/or other substituent groups.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods*, 2001, 23, 206-217; Gait et al., *Applications of Chemically synthesized RNA in RNA:Protein Interactions*, Smith, Ed., 1998, 1-36; Gallo et al., *Tetrahedron*, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl](FPMP), 2'-O—[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O—[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O[1(2-fluorophenyl)-4-ethoxypiperidin-4-yl].

In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

As used herein, "expression" refers to the process by which a gene ultimately results in a protein. Expression includes, but is not limited to, transcription, splicing, post-transcriptional modification, and translation.

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature*, 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.*, 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature*, 2001, 411, 494-498; Nishikura et al., *Cell*, 2001, 107, 415-416; and Bass et al., *Cell*, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the 2'-thio bicyclic nucleosides provided herein and may also include other monomer subunits including but not limited to nucleosides, modified nucleosides and nucleosides comprising sugar surrogate groups.

While in certain embodiments, oligomeric compounds provided herein can be utilized as described, the following examples serve only to illustrate and are not intended to be limiting.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3-H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the 16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3-H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

Lipofectin™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+mRNA Isolation

Poly(A)+mRNA is isolated according to Miura et al., (Clin. Chem., 1996, 42, 1758-1764). Other methods for poly (A)+mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
Forward primer:
AATGGCTAAGTGAAGATGACAATCAT    (SEQ ID NO: 2)

Reverse primer:
TGCACATATCATTACACCAGTTCGT     (SEQ ID NO: 3)
```

And the PCR probe:

FAM-TTGCAGCAATTCACTGTAAAGCTG-GAAAGG-TAMRA (SEQ ID NO: 4), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 7

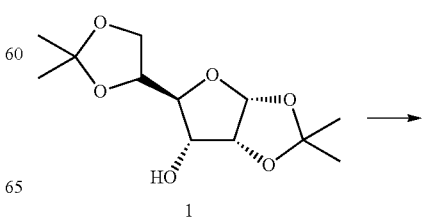

1

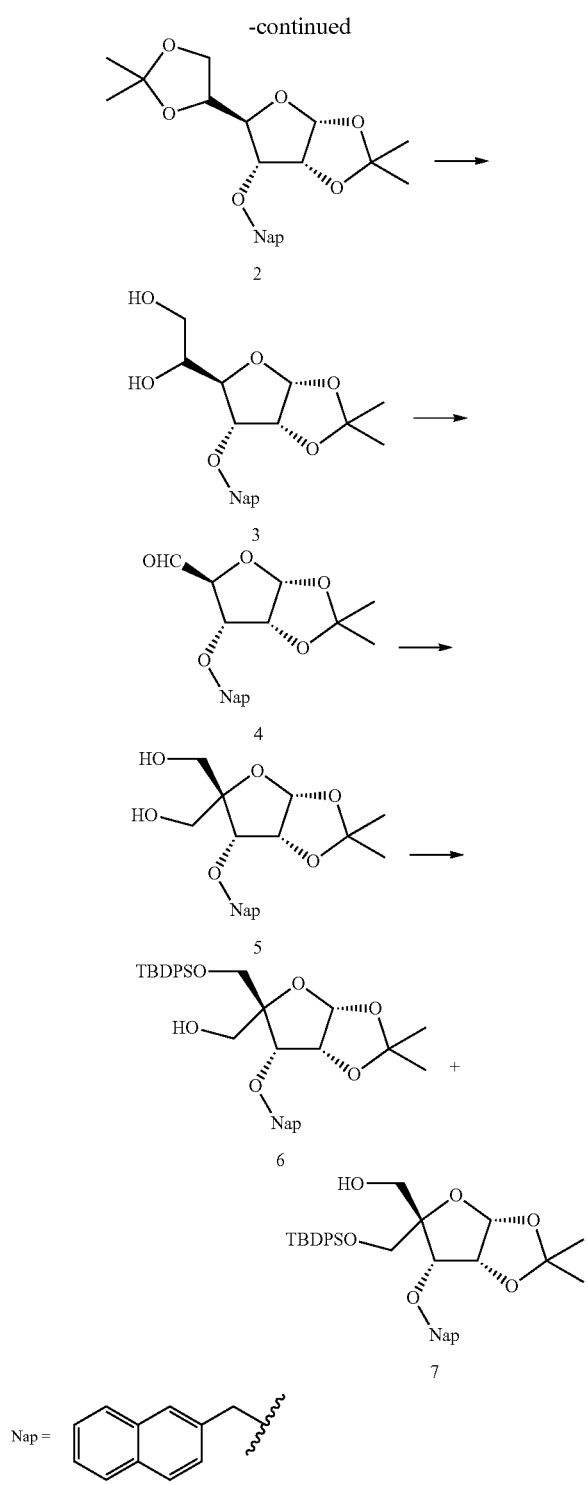

a) Preparation of Compound 2

Commercially available 1,2;5,6-di-O-isopropylidene-α-D-allofuranose, Compound 1, (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more sugar (Compound 1). The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 2 (206.0 g, 99%) as an off-white solid. $^1$H NMR (300 MHz, CDCl$_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

b) Preparation of Compound 3

Compound 2 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 2. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution and brine then dried (Na$_2$SO$_4$), filtered and concentrated under reduced pressure to provide Compound 3 as a yellow foam, which was used without any further purification.

c) Preparation of Compound 4

A solution of NaIO$_4$ (107.0 g) in water (3 L) was added over 40 minutes to a stirred (mechanical stirrer) solution of Compound 3 (crude from above) in dioxane (1.5 L). After 60 minutes the reaction mixture was poured into EtOAc (1.5 L) and the organic layer was separated, washed with water (1 L) and brine (1 L) then dried (Na$_2$SO$_4$) and concentrated to provide Compound 4 as a yellow oil, which was used without any further purification.

d) Preparation of Compound 5

Compound 4 (crude from above) was dissolved in a mixture of THF (500) and water (500 mL) and the reaction was cooled in an ice bath. 2N NaOH (600 mL) and formaldehyde (250 mL of a 37% aqueous solution) were added to the reaction with stirring at room temperature for 3 days. The reaction was then poured into EtOAc (1 L) and washed with water (1 L) and brine (1 L) then evaporated under reduced pressure until approximately 200 mL of EtOAc was left (a white precipitate was formed in the process). Hexanes (300 mL) was added to the precipitate and the mixture was allowed to stand for 16 hours after which the white solid was collected by filtration, washed with hexanes and dried under high vacuum over $P_2O_5$ to provide Compound 5 as a white solid (124 g, 66% from Compound 3). $^1$H NMR (300 MHz, CDCl$_3$) δ: 7.85 (m, 4H), 7.48 (m, 3H), 5.75 (d, 1H, J=3.9), 4.96 (d, 1H. J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

e) Preparation of Compounds 6 and 7 tert-Butyldiphenylchlorosilane (305.0 mmol, 84.0 mL) was added to a cold (0° C.) stirring solution of Compound 5 (278.0 mmol, 100.0 g) and triethylamine (305 mmol, 43.0 mL) in dichloromethane (600 mL). After the addition was complete, the reaction was warmed to room temperature and the stirring was continued for 16 hours. MeOH (50 mL) was added (to quench the excess TBDPSCl) to the reaction and the stirring was continued for another 2 hours at room temperature. The reaction was then diluted with chloroform and the organic layer was washed with 10% HCl, saturated NaHCO₃, brine, dried (Na₂SO₄) and concentrated to provide a thick oil. Hexanes (150 mL) were added to the oil and the mixture was sonicated until a solution resulted. The solution was seeded with a small amount of Compound 6 (previously isolated by column chromatography). After standing for 16 hours additional hexanes were added to the thick slurry and the solid was collected by filtration. The solid was then resuspended in hexanes and stirred vigorously for 30 minutes. The solid was collected by filtration to provide Compound 6 (80.5, 48% g) after drying under high vacuum for 16 hours. The filtrates were combined and concentrated under reduced pressure. The resulting oil was redissolved in minimum amount of hexanes and purified by silica gel column chromatography (gradient of up to 20% EtOAc in hexanes). Fractions containing Compound 7 were combined and concentrated to provide purified Compound 7.

Compound 6 ¹H NMR (300 MHz, CDCl₃) δ: 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H).

Compound 7 ¹H NMR (300 MHz, CDCl₃) δ: 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

Example 14

Preparation of Compound 12

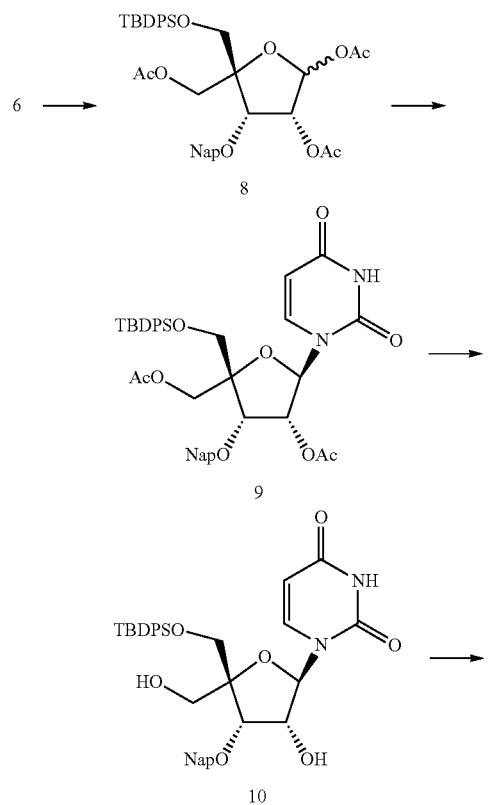

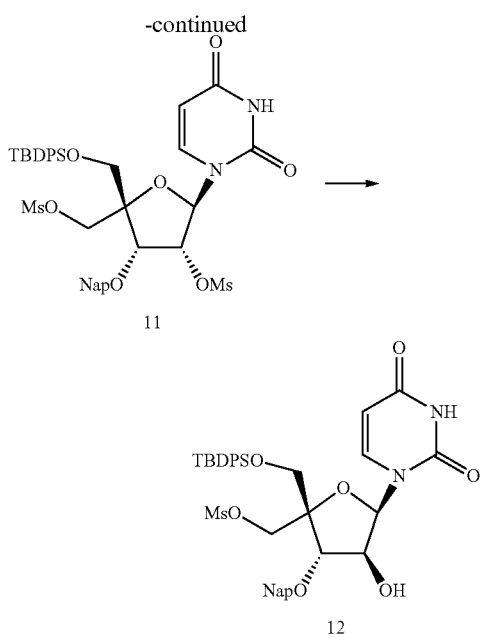

a) Preparation of Compound 8

Compound 6 was prepared as per the procedures illustrated in Example 13. Concentrated H₂SO₄ (2 drops) was added to a solution of Compound 6 (18 g, 30.06 mmol) in glacial acetic acid (88 mL) and acetic anhydride (22 mL). After stirring at room temperature for 2 hour, the reaction mixture was poured into ethyl acetate (300 mL) and the organic layer was washed with water (200 mL), saturated NaHCO₃ (200 mL), brine (200 mL), dried (Na₂SO₄) and concentrated under reduced pressure. Purification by column chromatography (SiO₂, eluting with 20% to 33% ethyl acetate/hexanes) provided Compound 8 (18.53 g, 90%, a/β mixture, 4:1). ¹H NMR (Major isomer, 300 MHz, CDCl₃) δ 7.85-7.31 (m, 17H), 6.19 (s, 1H), 7.30 (m, 6H), 5.43 (d, J=5.1 Hz, 1H), 4.978-4.68 (m, 2H), 4.56-4.51 (m, 3H), 3.68 (m, 2H), 2.12 (s, 3H), 1.96 (s, 3H), 1.04 (s, overlapping with other isomer, 9H,); MS (ES) m/z 707.1 [M+Na]⁺.

b) Preparation of Compound 9

Compound 8 (18 g, 26.30 mmol) was mixed with uracil (5.90 g, 52.6 mmol) and dried over P₂O₅ under reduced pressure over night. The reaction mixture was suspended in anhydrous CH₃CN (113 mL) and N,O-Bis(trimethylsilyl)acetamide (38.58 mL, 117.80 mmol) added. After heating at 67° C. for 1.5 h to get a clear solution, the reaction mixture was cooled to 0° C. To this trimethylsilyl triflate (9.52 mL, 52.60 mmol) was added. The reaction mixture was stirred at 0° C. for 15 min then heated at 70° C. for 1.5 h. The reaction mixture was cooled to room temperature and poured into ethyl acetate (200 mL). The organic layer was washed with saturated NaHCO₃ (100 mL), brine (100 mL), dried (Na₂SO₄) and concentrated under reduced pressure. The residue was purified by flash silica gel column chromatography and eluted with 5% methanol in CH₂Cl₂ to provide Compound 9 (16.85 g, 87%). ¹H NMR (300 MHz, CDCl₃) δ 8.22 (brs, 1H), 7.63-7.08 (m, 18H), 5.98 (d, J=4.9 Hz, 1H), 5.22 (t, J=5.3 Hz, 1H), 5.14 (d, J=7.9 Hz, 1H), 4.54 (d, J=11.5 Hz, 1H), 4.38-4.26 (m, 3H), 3.87 (d, J=12.4 Hz, 1H), 3.70 (d, J=11.3 Hz, 1H), 3.49 (d, J=11.3 Hz, 1H), 1.88 (s, 3H), 1.70 (s, 3H), 0.82 (s, 9H); $^{13}$C NMR (75 MHz, CDCl$_3$) δ 170.6, 170.3, 162.91, 150.2, 140.2, 134.6, 133.4, 132.8, 132.1, 130.5, 130.4, 128.6, 128.2, 128.0, 127.0, 126.6, 126.5, 125.8, 103.1, 87.5, 87.0, 77.4, 77.1, 74.9, 65.0, 63.3, 27.2, 20.9, 19.5; MS (ES) m/z 735.1 [M−]$^−$.

c) Preparation of Compound 10

Compound 9 (16.7 g, 22.66) was dissolved in methanolic ammonia (7 M, 123 mL). The reaction mixture was stirred at room temperature for 18 h. Solvent was removed under reduced pressure and the residue was purified by column chromatography and eluted with 5% methanol in dichloromethane to yield Compound 10 (14.18 g, 96%). $^1$HNMR (300 MHz, DMSO-d$_6$) δ 11.35 (s, 1H), 7.94-7.89 (m, 4H), 7.59-7.30 (m, 14H), 5.95 (d, J=5.1 Hz, 1H), 5.74 (d, J=7.4 Hz, 1H), 5.17 (d, J=7.9 Hz, 1H), 5.04 (t, J=5.9 and 5.1 Hz, 1H), 4.97 (d, J=12.0 Hz, 1H), 4.69 (d, J=12.1 Hz, 1H), 4.4-4.38 (m, 1H), 4.26 (d, J=5.9 Hz, 1H), 3.81-3.69 (m, 3H) 3.59-3.53 (m, 1H), 0.93 (s, 9H), $^{13}$C NMR (75 MHz, CDCl$_3$) δ 163.7, 151.2, 140.3, 135.7, 135.5, 134.9, 133.4, 133.3, 132.9, 132.2, 130.3, 130.2, 128.6, 128.2, 128.1, 127.9, 127.2, 126.4, 126.3, 126.1, 102.7, 91.4, 89.2, 76.4, 75.0, 73.5, 65.1, 63.0, 27.1, 19.5; MS (ES) m/z 650.9 [M−H]$^−$.

d) Preparation of Compound 11

Compound 10 (14 g, 21.46 mmol) was dried over P$_2$O$_5$ under reduced pressure. Methanesulfonyl chloride (7.51 mL, 96.68 mmol) was added to a cold (0° C.) solution of Compound 10 in anhydrous pyridine (118 mL). After stirring at room temperature for 3 h, the reaction mixture was poured into ethyl acetate and the organic layer was sequentially washed with saturated NaHCO$_3$ (400 mL), brine (400 mL), dried (Na$_2$SO$_4$) and concentrated under vacuum. The residue obtained was purified using flash silica gel column chromatography and eluted with 5% MeOH in CH$_2$Cl$_2$ to provide Compound 11 (16.21 g, 93% yield). $^1$H NMR (300 MHz, CDCl$_3$) δ 8.33 (s, 1H), 7.86-7.79 (m, 4H), 7.58-7.28 (m, 14H), 6.13 (d, J=3.6 Hz, 1H), 5.38 (m, 1H), 5.31 (d, J=8.1 Hz, 1H), 4.96 (d, J=11.5 Hz, 1H), 4.65 (d, J=11.3 Hz, 1H), 4.57-4.53 (m, 2H), 4.23 (d, J=11.5 Hz, 1H), 3.98 (d, J=11.3 Hz, 1H) 3.77 (d, J=11.3 Hz, 1H), 3.18 (s, 3H), 2.84 (s, 3H), 1.05 (s, 9H); MS (ES) m/z 806.9 [M−H]$^−$.

e) Preparation of Compound 12

To a solution of Compound 11 (16.00 g, 19.74 mmol) in anhydrous CH$_3$CN (135 mL) was added 1,8-diazabicyclo[5.4.0]undec-7-ene (5.46 mL, 39.48 mmol). After stirring at room temperature for 3 h, the mixture was diluted with EtOAc (300 mL), washed with 1% (v/v) aqueous acetic acid (1×400 mL) and brine (2×400 mL), dried over anhydrous Na$_2$SO$_4$, filtered, and evaporated to a foam. The foam was redissolved in 1,4-dioxane (216 mL) and 2 M aqueous NaOH (54 mL) was added. After 45 min, the mixture was neutralized with AcOH, diluted in ethyl acetate (400 mL), washed with saturated aqueous NaHCO$_3$ (1×300 mL) and brine (300 mL), dried over anhydrous Na$_2$SO$_4$, filtered, and evaporated. Purification by silica gel chromatography (5% MeOH in CH$_2$Cl$_2$) yielded Compound 12 (12.25 g, 84.8% yield) as a white foam. $^1$H NMR (300 MHz, DMSO-d$_6$) δ 11.33 (s, 1H), 7.91 (br s, 4H), 7.59-7.34 (m, 14H), 6.22 (d, J=4.9 Hz, 1H), 6.02 (d, J=4.7 Hz, 1H), 5.16 (d, J=8.1 Hz, 1H), 4.97 (d, J=12.2 Hz, 1H), 4.79 (d, J=12.2 Hz, 1H), 4.58-4.50 (m, 2H), 4.40 (d, J=10.4 Hz, 1H), 4.34 (br s, 1H) 3.84 (m, 2H), 3.16 (s, 3H), 0.85 (s, 9H); MS (ES) m/z 731.2 [M+H]$^+$.

Example 15

Preparation of Compound 17

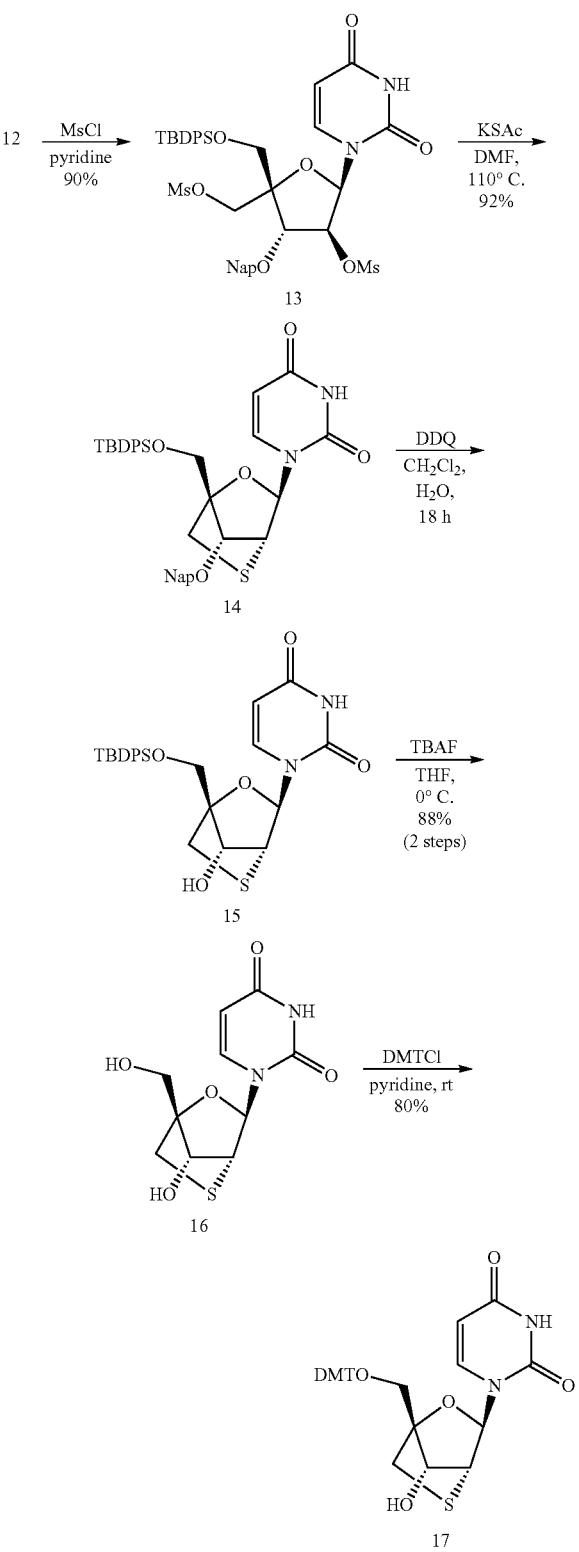

Compound 12 was prepared as per the procedures illustrated in Example 14. The structure of Compound 17 was confirmed by spectral analysis, ¹H NMR and mass spectroscopy.

Example 16

Preparation of Compound 19

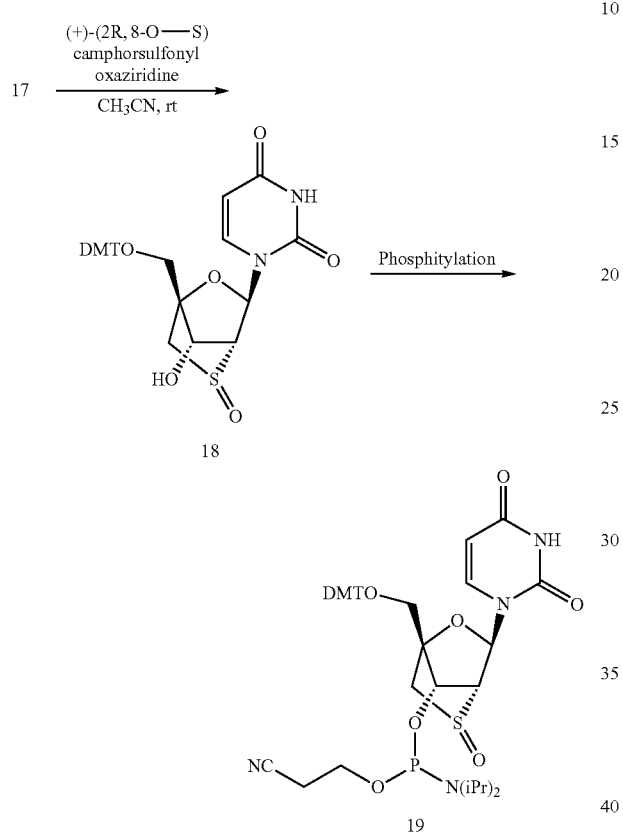

Compound 17 is prepared as per the procedures illustrated in Example 15.

Example 17

Preparation of Compound 23

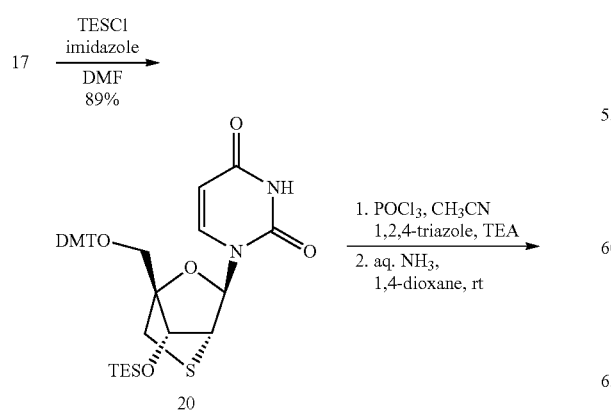

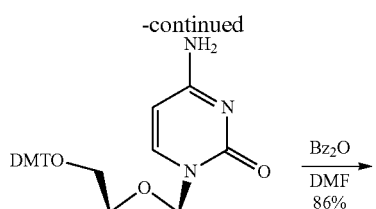

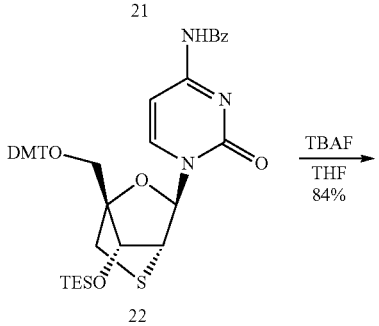

Compound 17 was prepared as per the procedures illustrated in Example 15. Compound 23 was prepared as per the procedures illustrated above (Example 17) and confirmed by spectral analysis, ¹H NMR and mass spectroscopy.

Example 18

Preparation of Compound 25

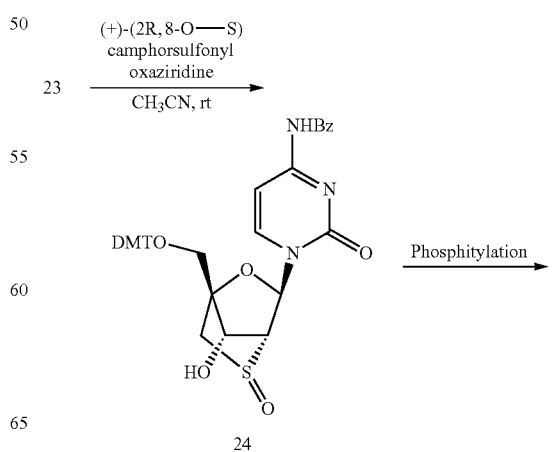

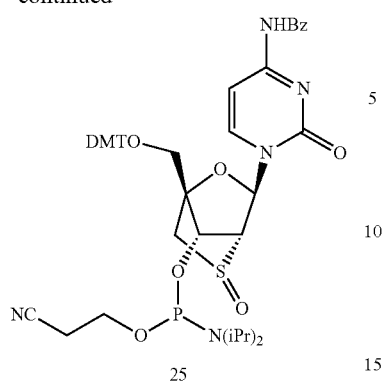

25 a) Preparation of Compound 24

Compound 23 was prepared as per the procedures illustrated in Example 17. Compound 23 (0.85 g, 1.23 mmol) was dissolved in anhydrous acetonitrile (6.1 mL) and (1S)-(+)-10-(camphorsulfonyl)oxaziridine (0.49 g, 2.13 mmol) was added. The mixture was stirred at room temperature for 18 h. The reaction mixture was concentrated under reduced pressure to obtain the crude residue, which was then purified by silica gel column chromatography (50% EtOAc in hexanes) to yield Compound 24 (0.46 g, 53%). $^1$H NMR (300 MHz, CDCl$_3$): δ 13.20 (s, 1H), 8.31-7.94 (br s, 2H), 7.87 (s, 1H), 7.61-7.01 (m, 13H), 6.96-6.69 (m, 4H), 6.19 (s, 1H), 4.99 (s, 2H), 4.51 (s, 1H), 3.62-3.30 (m, 3H), 2.47 (d, J=1.0 Hz, 1H), 1.63 (s, 3H). ES MS m/z 708.2 [M+H]$^+$.

b) Preparation of Compound 25

Compound 24 (0.43 g, 0.60 mmol) was dried over P$_2$O$_5$ under reduced pressure, then dissolved in anhydrous DMF (2.6 mL). 1-H-tetrazole (0.037 g, 0.53 mmol), N-methylimidazole (0.018 mL, 0.22 mmol) and 2-cyanoethyl-N,N,N',N'-tetraisopropylphosphorodiamidite (0.29 mL, 0.90 mmol) were then added. After 3 hours, EtOAc (50 mL) was added and the mixture was washed with aqueous NaHCO$_3$ (50 mL) and brine (50 mL) then dried over anhydrous Na$_2$SO$_4$, filtered and evaporated in vacuo to give an oil. The oily residue was purified by silica gel column chromatography (50% EtOAc in hexanes) to yield Compound 25 (0.46 g, 85%) as a white foam. MS (ES): m/z 906.2 [M−H]$^−$. $^{31}$P NMR (121 MHz, CDCl$_3$): δ 150.9, 150.8.

Example 19

Preparation of Compound 35

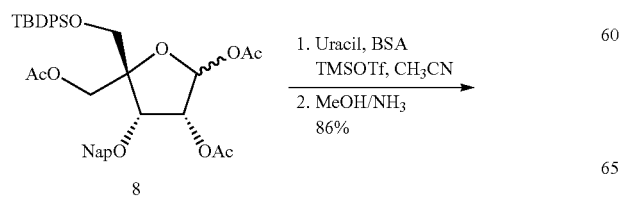

8

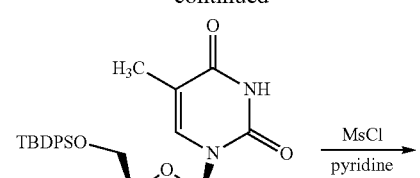

26

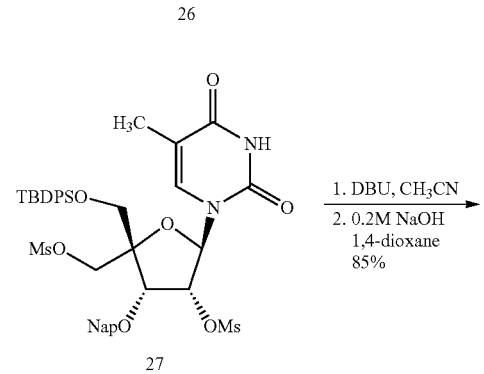

27

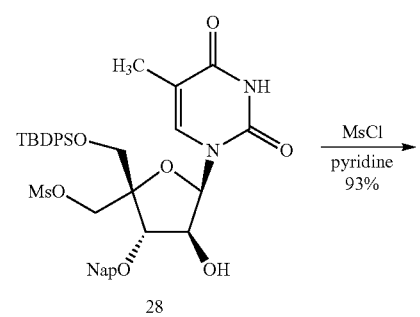

28

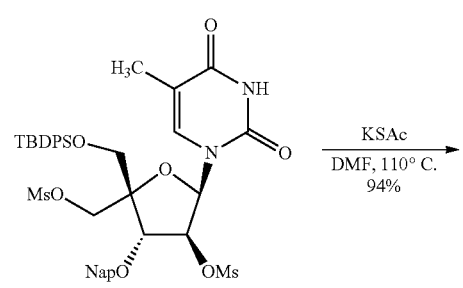

29

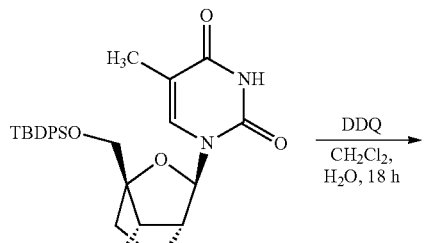

30

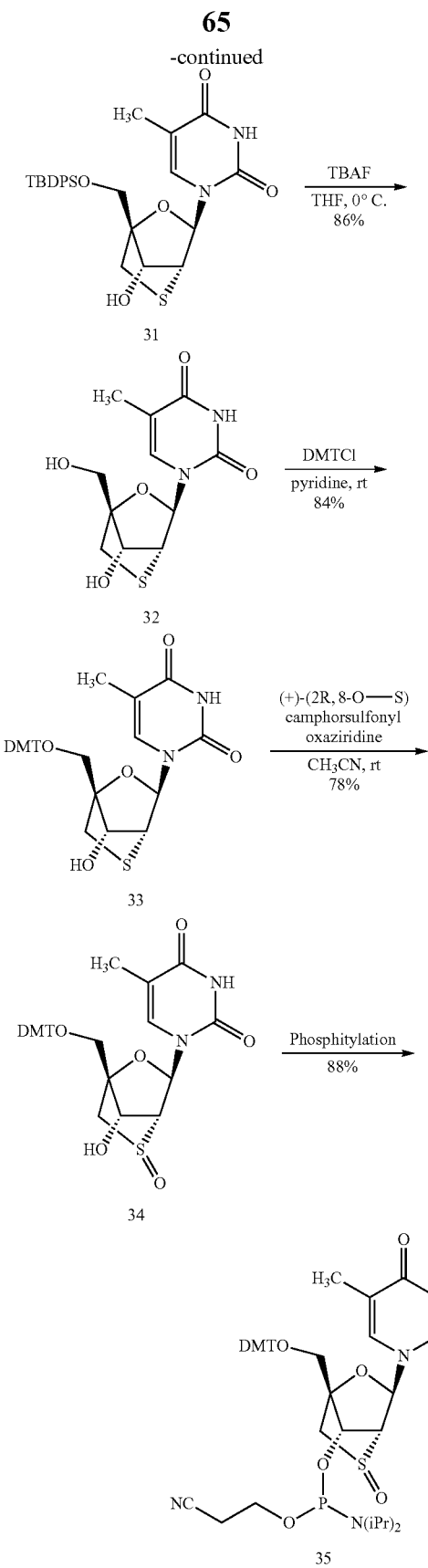

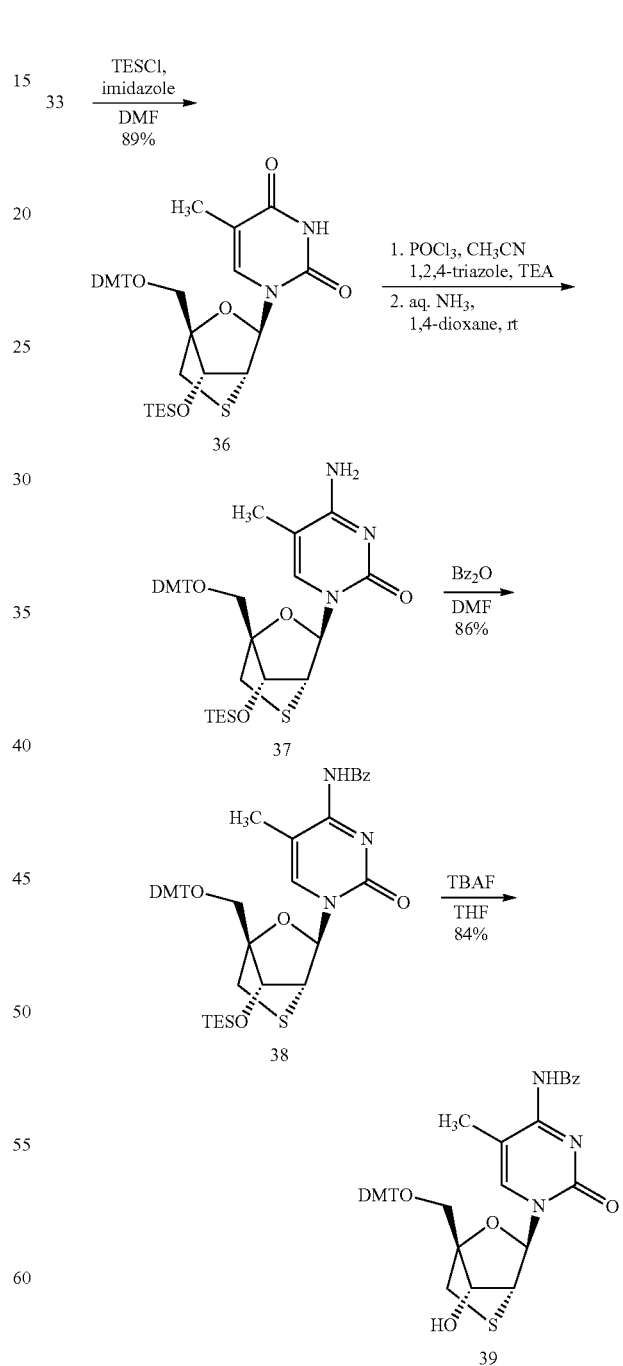

cedures illustrated above (Example 19) and confirmed by spectral analysis, $^1$H NMR and mass spectroscopy. An alternative method for the preparation of Compound 27 was reported by Pedersen, D. S.; Koch, T. *Synthesis* 2004, 4, 578-582.

Example 20

Preparation of Compound 39

Compound 8 was prepared as per the procedures illustrated in Example 14. Compound 35 was prepared as per the pro- Compound 33 was prepared as per the procedures illustrated in Example 19. Compound 39 was prepared as per the procedures illustrated above (Example 20) and confirmed by spectral analysis, $^1$H NMR and mass spectroscopy.
Example 21
Preparation of Compound 41
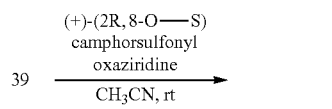
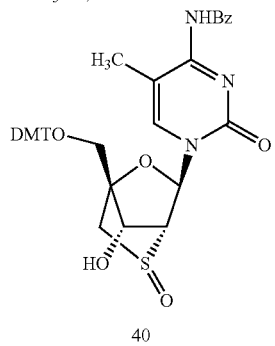
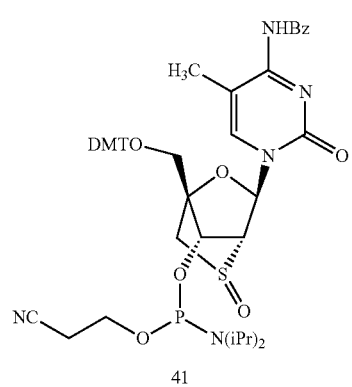
Compound 39 is prepared as per the procedures illustrated in Example 20.
Example 22
Preparation of Compound 52
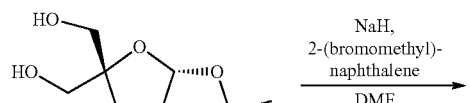
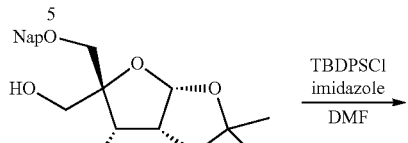
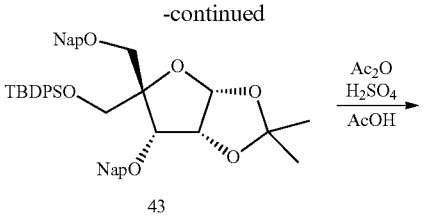
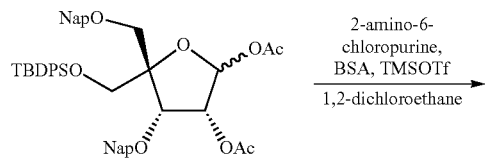
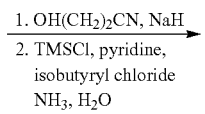
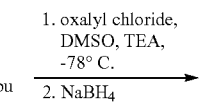
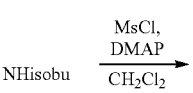

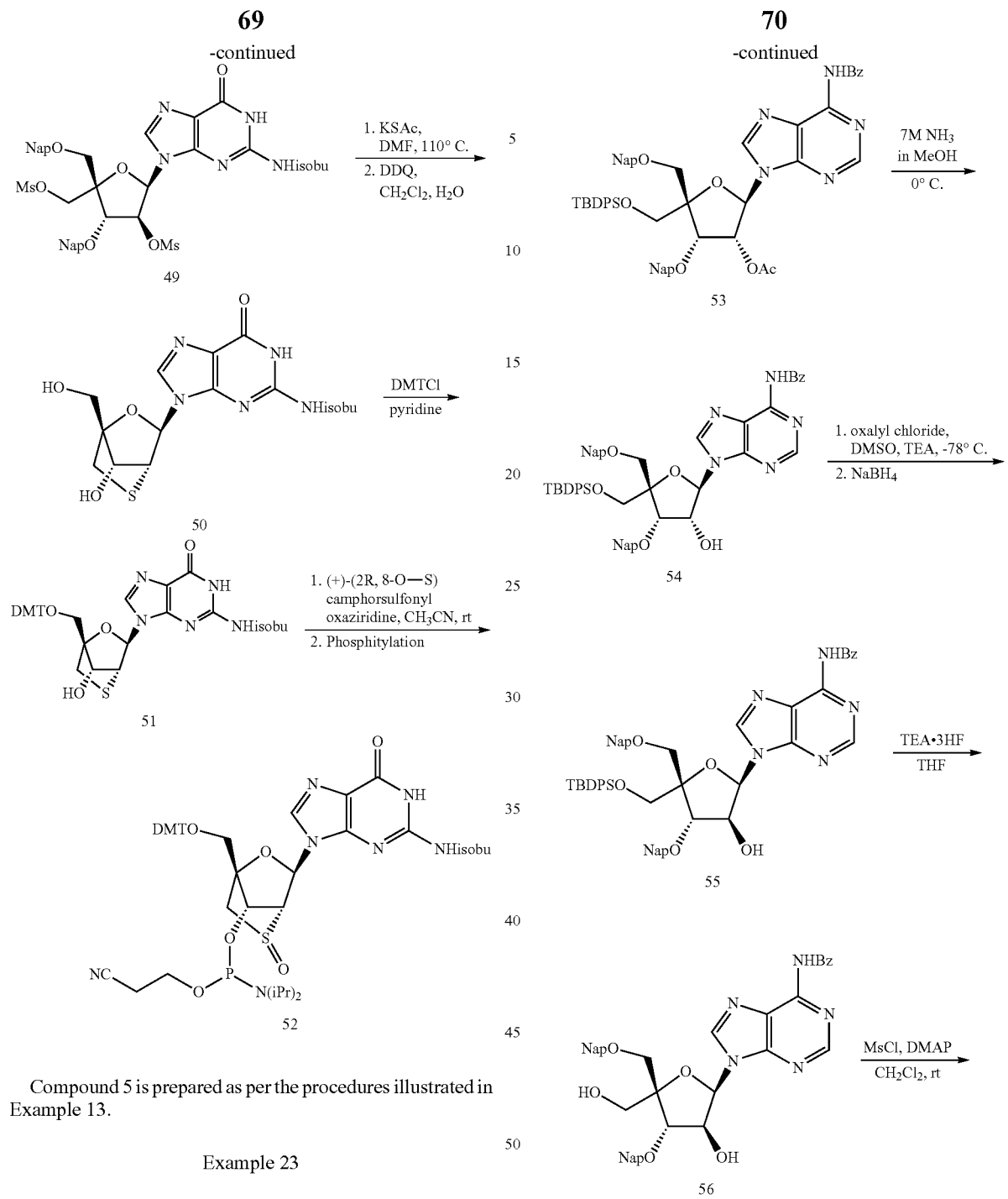
Compound 5 is prepared as per the procedures illustrated in Example 13.
Example 23
Preparation of Compound 60
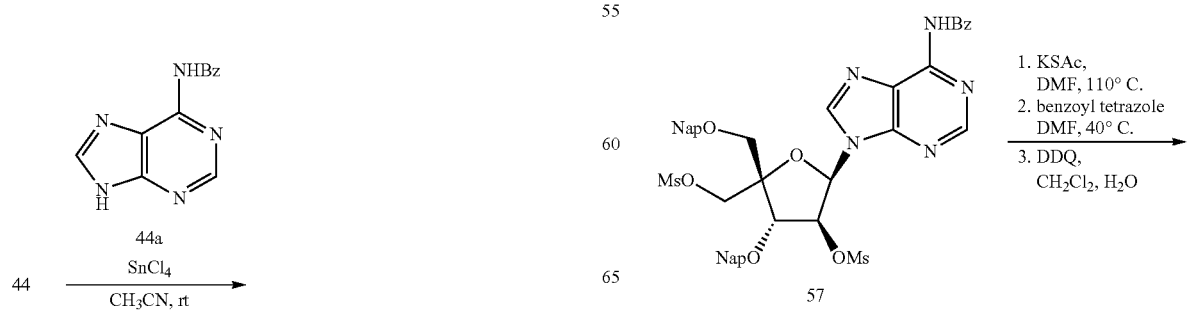

71
-continued
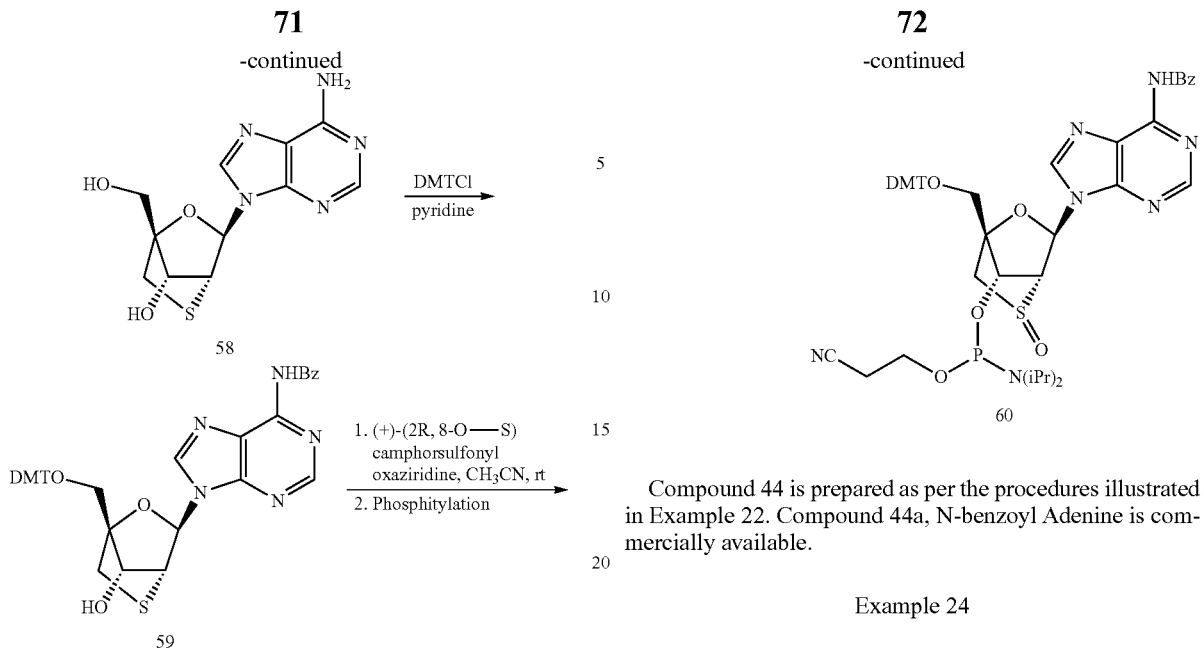
Compound 44 is prepared as per the procedures illustrated in Example 22. Compound 44a, N-benzoyl Adenine is commercially available.
Example 24
Preparation of Compound 63
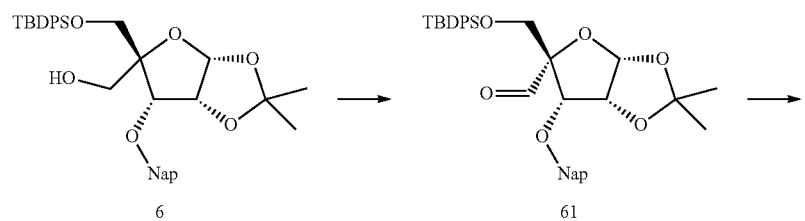
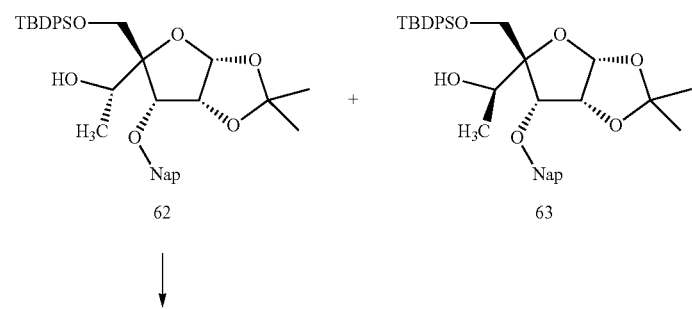
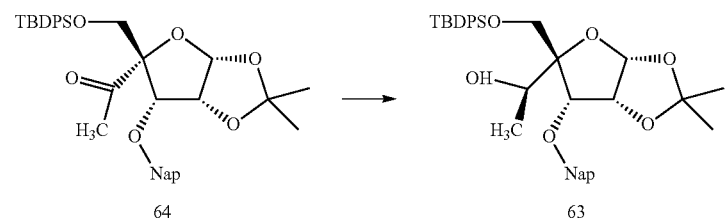

a) Preparation of Compound 61

Compound 6 was prepared as per the procedures illustrated in Example 13. Dimethylsulfoxide (10.8 mL, 152.0 mmol) was added dropwise to a cold (−78° C.) solution of oxalyl chloride (6.7 mL, 76.0 mmol) in dichloromethane (400 mL). After stirring for 30 min, a solution of Compound 6 (34.2 g, 56.4 mmol) in dichloromethane (40 mL) was added to the reaction mixture. The stirring was continued for 45 min at −78° C. and triethylamine (31.4 mL, 224.0 mmol) was added. After stirring for 15 min at −78° C., the ice bath was removed and the reaction was allowed to gradually warm to rt over 45 min. The reaction was diluted with dichloromethane and the organic phase was sequentially washed with 5% aqueous HCl, saturated sodium bicarbonate, brine, then dried over $Na_2SO_4$ and concentrated in vacuo to provide Compound 61, which was used without any further purification.

b) Preparation of Compounds 62 and 63

A suspension of cerium III chloride (9.2 g, 37.5 mmol) in THF (400 mL) was stirred at rt for 60 min. The reaction was cooled in an ice bath and methyl magnesium bromide (75.0 mL of a 1.0 M solution in THF) was added over 5 min. After stirring at 0° C. for 90 min, the reaction was cooled to −78° C. and a solution of crude aldehyde, Compound 61 in THF (75 mL) was added to the reaction mixture. After 3 h at −78° C., the reaction was allowed to gradually warm to rt and carefully quenched with saturated ammonium chloride. The reaction was diluted with ethyl acetate and the organic layer was sequentially washed with 5% HCl, saturated sodium bicarbonate, brine, then dried over $Na_2SO_4$ and concentrated under reduced pressure. The resulting residue was purified using silica gel column chromatography eluting with 10 to 30% ethyl acetate in hexanes to provide the pure alcohol, Compound 62 (7.4 g, 21% from Compound 6) and a mixture of Compounds 62 and 63 (26.3 g, 76% from Compound 6, Compounds 62:63=10:1) was recovered as viscous oils.

Compound 62 $^1$H NMR (300 MHz, $CDCl_3$) δ: 7.89-7.79 (m, 4H), 7.65-7.26 (m, 13H), 5.84 (d, J=3.6 Hz, 1H), 5.05 (d, J=11.5 Hz, 1H), 4.83-4.53 (m, 4H), 3.91 (d, J=11.1 Hz, 1H), 3.84 (d, J=11.1 Hz, 1H), 3.36 (s, 1H), 1.63 (s, 3H), 1.39 (s, 3H), 1.10 (d, J=6.6 Hz, 3H), 0.91 (s, 9H). $^{13}$C NMR (75 MHz, $CDCl_3$) δ: 135.6, 135.5, 134.4, 133.3, 133.3, 133.2, 133.1, 129.7, 129.7, 128.7, 128.0, 127.8, 127.7, 127.7, 127.2, 126.4, 126.3, 125.7, 113.8, 104.8, 88.6, 79.4, 78.3, 73.0, 68.8, 62.4, 27.1, 26.8, 26.7, 19.2, 16.1. ESI-MS m/z: $[M+Na]^+$ found 635.2. calcd 635.2907.

Compound 63 $^1$H NMR (300 MHz, $CDCl_3$) δ: 7.88-7.78 (m, 4H), 7.61-7.27 (m, 13H), 5.87 (d, J=3.6 Hz, 1H), 4.96 (d, J=12.1 Hz, 1H), 4.74 (t, 1H), 4.66 (d, J=12.1 Hz, 1H), 4.54 (d, J=5.3 Hz, 1H), 4.32-4.18 (m, 1H), 3.69 (d, J=10.7 Hz, 1H), 3.52 (d, J=10.7 Hz, 1H), 3.12 (s, 1H), 1.69 (s, 3H), 1.39 (s, 3H), 1.11 (d, J=6.4 Hz, 3H), 0.90 (s, 9H). $^{13}$C NMR (75 MHz, $CDCl_3$) δ: 135.5, 134.8, 133.2, 133.2, 132.9, 132.8, 129.8, 129.7, 128.4, 127.9, 127.7, 126.9, 126.3, 126.1, 125.7, 114.3, 104.5, 90.4, 79.6, 78.1, 72.8, 67.1, 64.6, 26.9, 26.7, 19.1, 17.0. ESI-MS m/z: $[M+Na]^+$ found 635.2. calcd 635.2907.

c) An Alternative Method in the Preparation of Compound 63

Dimethylsulfoxide (37.9 mL, 489.0 mmol) was added dropwise to a cold (−78° C.) solution of oxalyl chloride (21.4 mL, 244.0 mmol) in dichloromethane (800 mL). After stirring for 30 min, a solution of Compound 62 (100.0 g, 163.0 mmol) in dichloromethane (200 mL) was added to the reaction mixture. The stirring was continued for 45 min at −78° C. and triethylamine (102.0 mL, 726.0 mmol) was added. After stirring at −78° C. for 15 min, the ice bath was removed and the reaction was allowed to gradually warm to rt over 45 min. The reaction was diluted with dichloromethane and the organic phase was sequentially washed with 10% citric acid solution, saturated sodium bicarbonate, brine, then dried over $Na_2SO_4$ and concentrated under reduced pressure to provide the crude ketone, Compound 64, which was used without any further purification.

A solution of lithium borohydride (122.0 mL of a 2M solution in THF, 244 mmol) was added drop-wise over 30 min to a cold (−78° C.) solution of Compound 64 (99.6 g, 163 mmol) in methanol (500 mL). After the addition was complete, the cooling bath was removed and the reaction was stirred for 2 h. The reaction was then cooled in an ice bath and carefully quenched with saturated $NH_4Cl$ solution and diluted with ethyl acetate. The organic layer was separated and sequentially washed with water, saturated sodium bicarbonate, brine, then dried over $Na_2SO_4$ and concentrated under reduced pressure. The resulting residue was purified using silica gel column chromatography eluting with 30% ethyl acetate in hexanes to furnish Compound 63 (97.2 g, 95%, Compounds 63:62>15:1) as a viscous oil. The spectroscopic analysis is identical to those reported above.

Example 25

Preparation of Compound 75

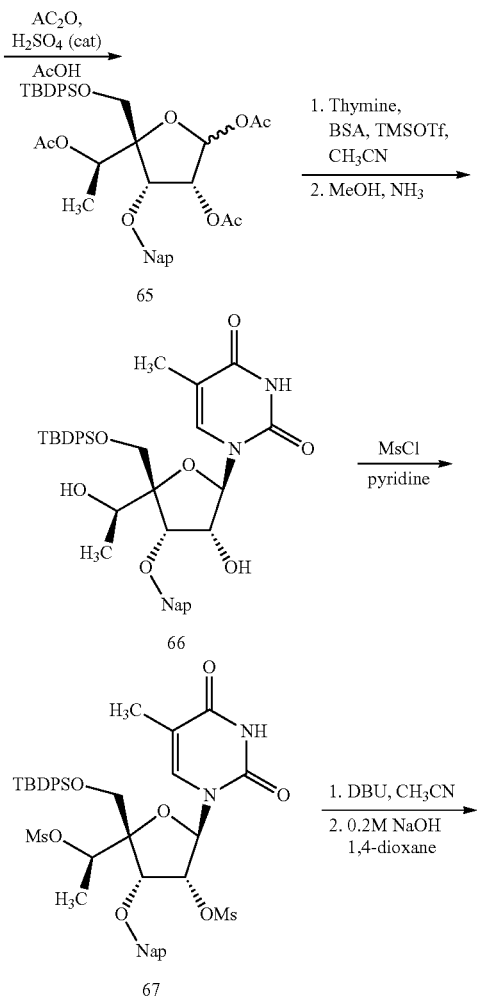

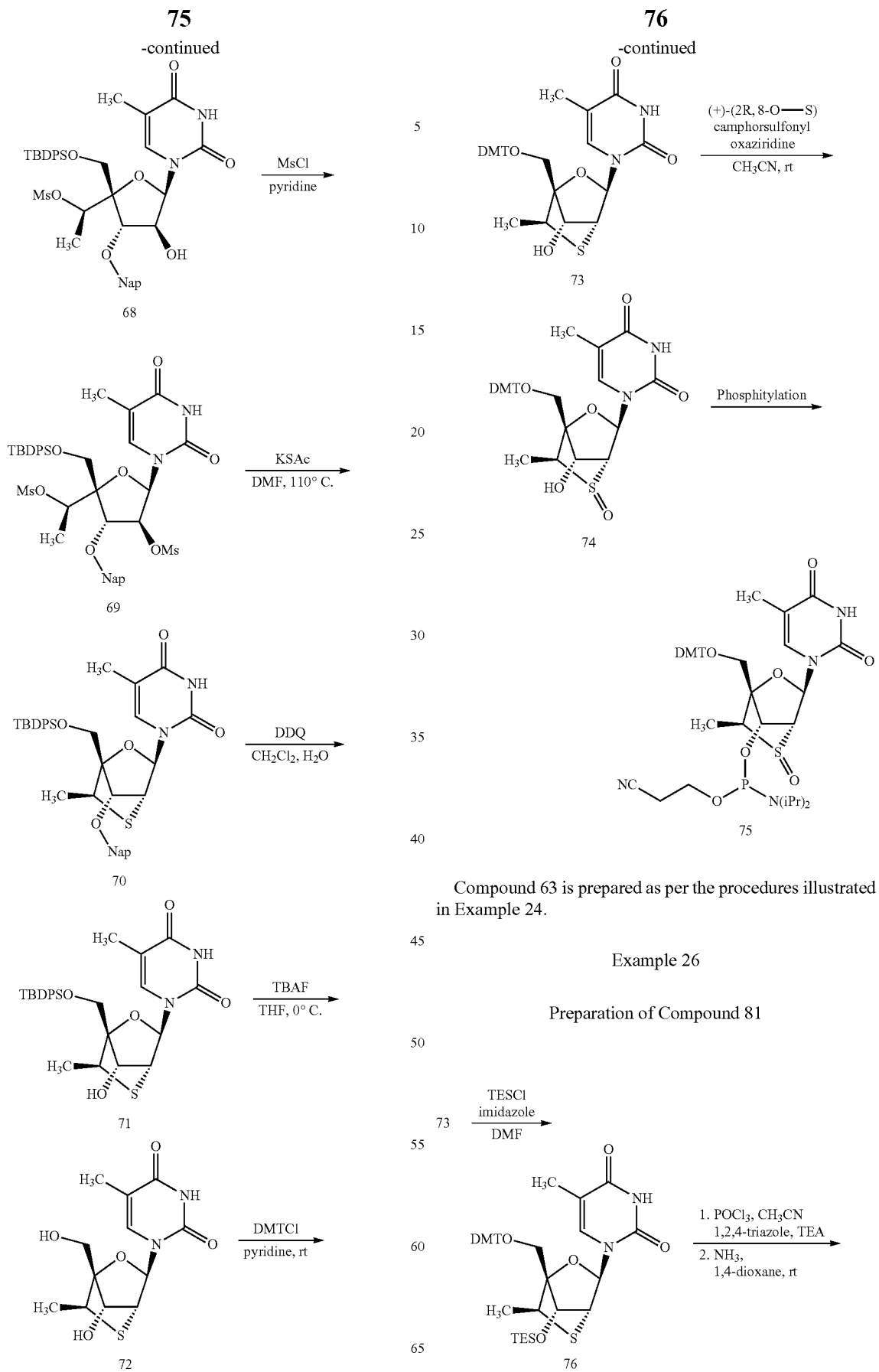
Compound 63 is prepared as per the procedures illustrated in Example 24.
Example 26
Preparation of Compound 81

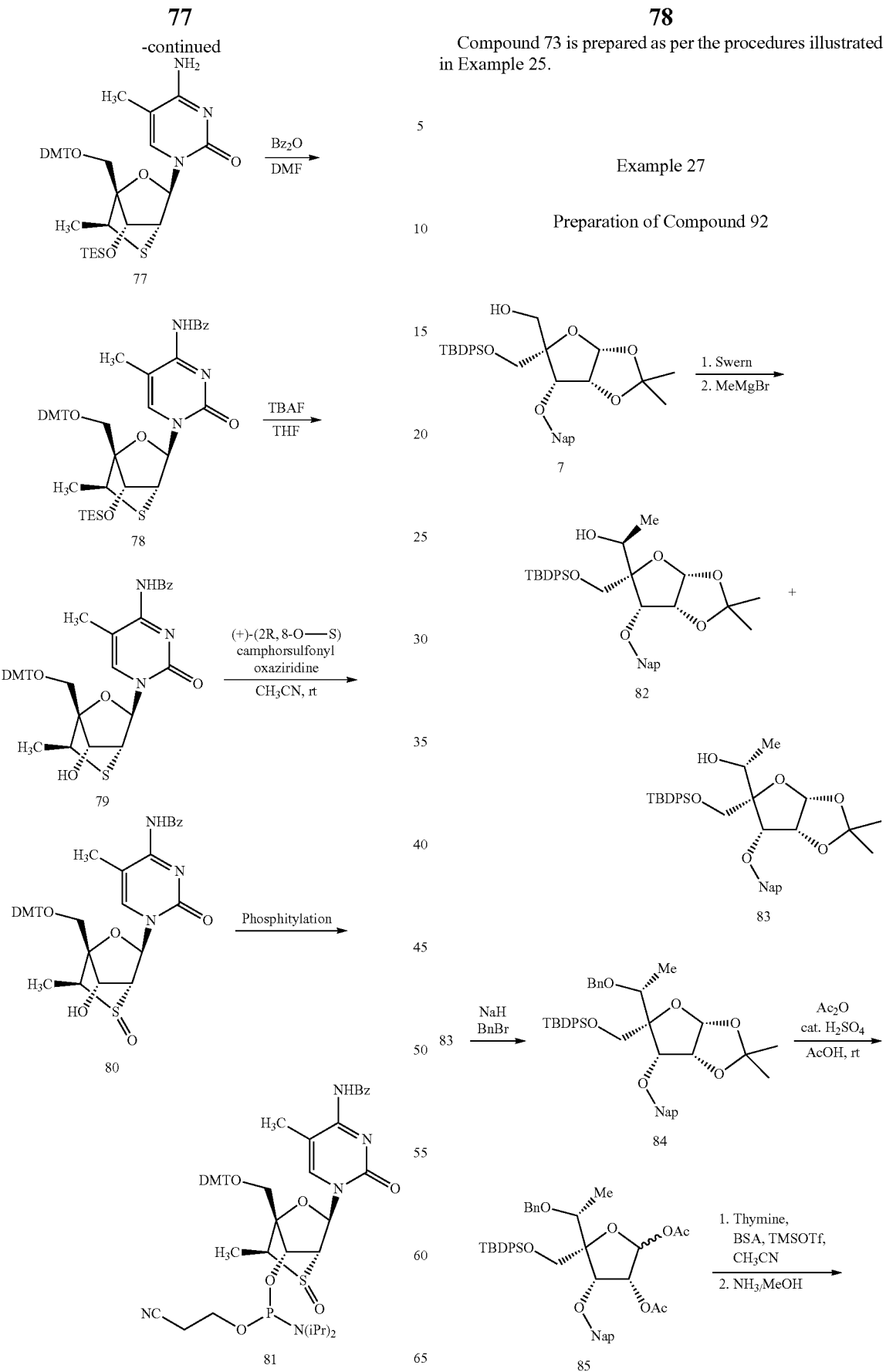
Compound 73 is prepared as per the procedures illustrated in Example 25.
Example 27
Preparation of Compound 92

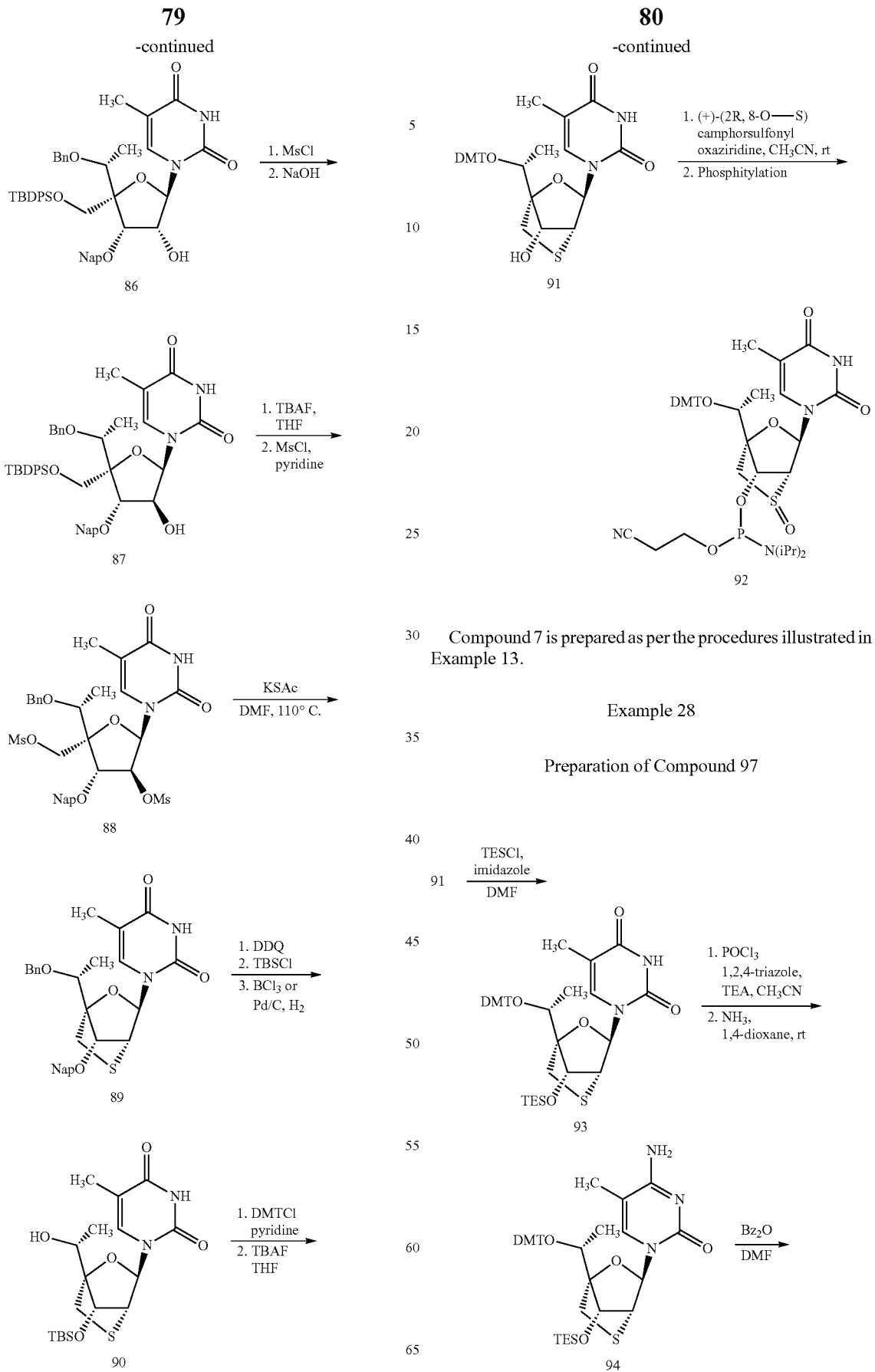
Compound 7 is prepared as per the procedures illustrated in Example 13.
Example 28
Preparation of Compound 97

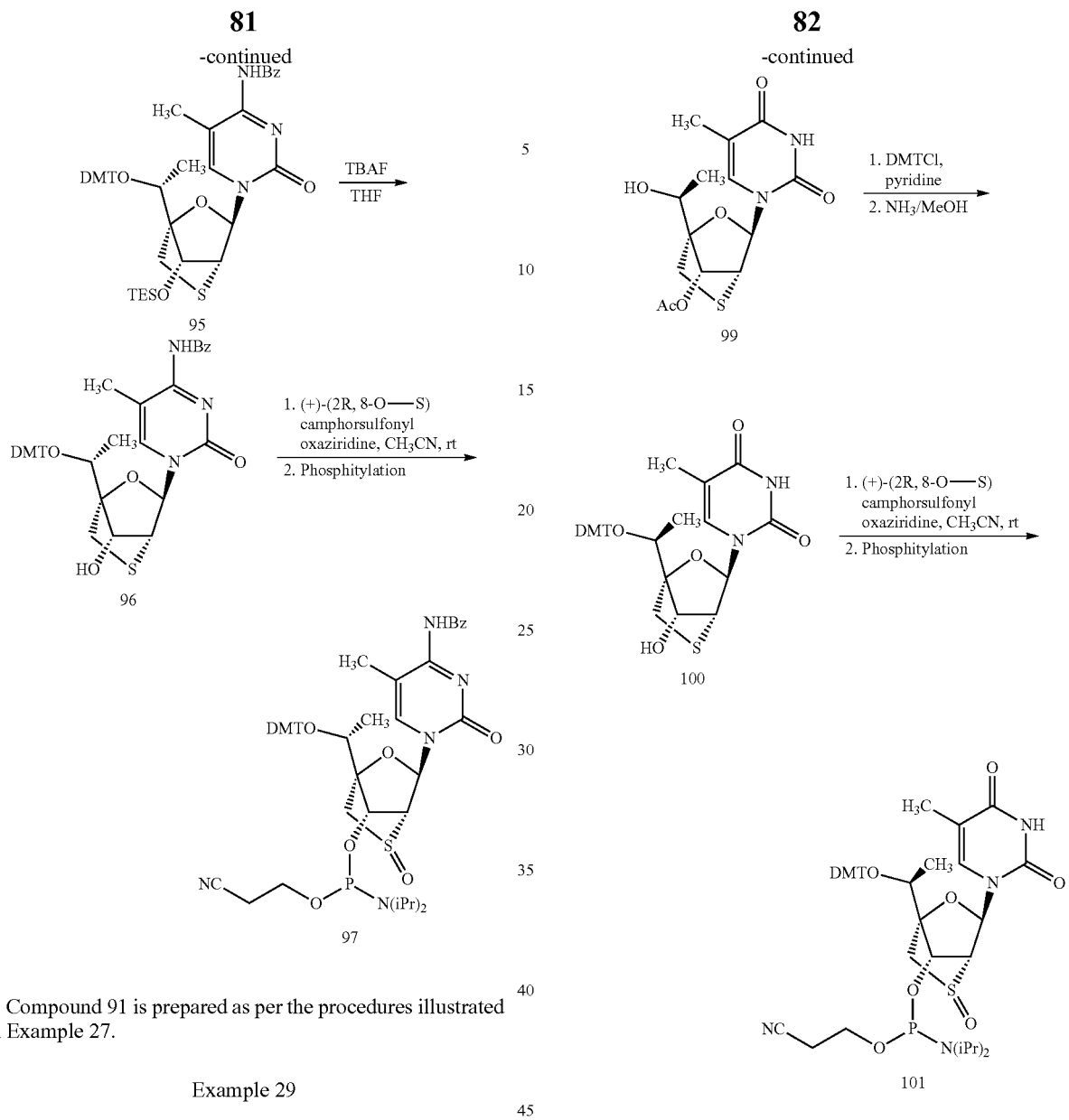
Compound 91 is prepared as per the procedures illustrated in Example 27.
Example 29
Preparation of Compound 101
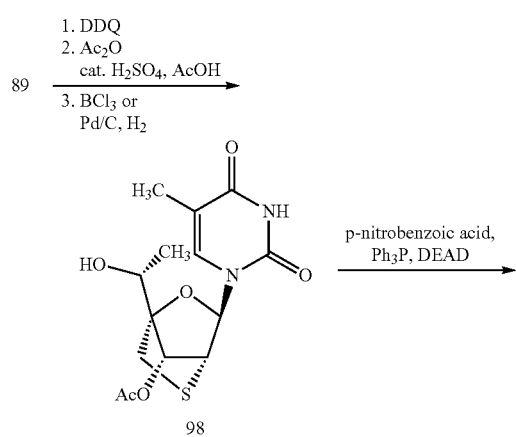
Compound 89 is prepared as per the procedures illustrated in Example 27.
Example 30
General Procedure for the Preparation of Compounds of Formula III
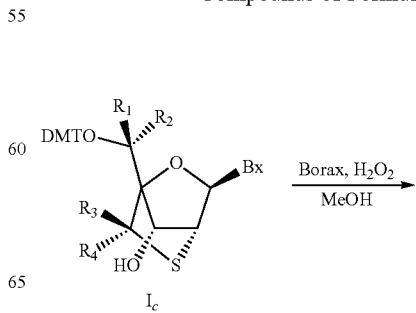

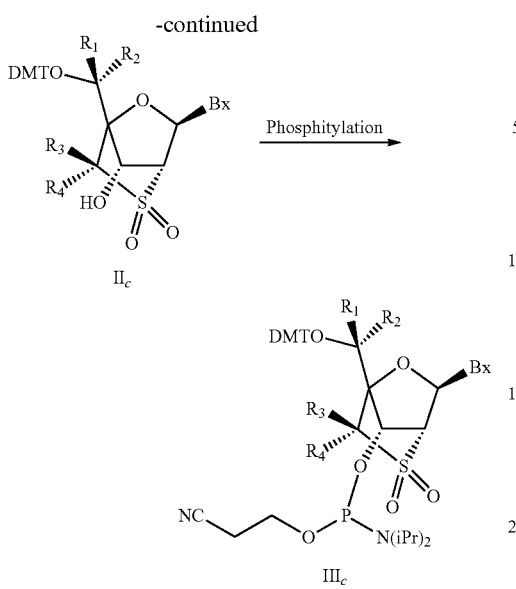

Bx is a heterocyclic base moiety;
$R_1$, $R_2$, $R_3$ and $R_4$ are each independently H or a substituent group.

In certain embodiments, compounds of Formula $I_c$ are prepared as per the procedures illustrated in Examples 15, 17, 19, 20, 22, 23, and 25-28. In certain embodiments, compounds of Formula $I_c$ are prepared using the procedures illustrated in the examples illustrated above and methods and procedures known in the art.

Example 31

$T_m$ Measurements

A Cary 100 Bio spectrophotometer with the Cary Win UV Thermal program was used to measure absorbance vs. temperature. For the $T_m$ experiments, oligonucleotides were prepared at a concentration of 8 µM in a buffer of 100 mM Na+, 10 mM phosphate, 0.1 mM EDTA, pH 7. Concentration of oligonucleotides were determined at 85° C. The oligonucleotide concentration was 4 µM with mixing of equal volumes of test oligonucleotide and match or mismatch RNA strand. Oligonucleotides were hybridized with the complimentary or mismatch RNA strand by heating duplex to 90° C. for 5 min and allowed to cool at room temperature. Using the spectrophotometer, $T_m$ measurements were taken by heating duplex solution at a rate of 0.5 C/min in cuvette starting @15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program.

Example 32

Preparation of Oligomeric Compounds

Following synthetic procedures well know in the art, some of which are illustrated herein, oligomeric compounds are prepared having at least one substituted 2'-sulfoxide or 2'-sulfone bicyclic nucleosides, using one or more of the phosphoramidite compounds illustrated in the Examples such as DMT phosphoramidites (see Compound 19, Example 16, Compound 25, Example 18, Compound 35, Example 19, Compound 41, Example 21, Compound 52, Example 22, Compound 60, Example 23, Compound 75, Example 25, Compound 81, Example 26, Compound 92, Example 27, Compound 97, Example 28, Compound 101, Example 20 and Compounds of Formula III, Example 30).

Example 33

$T_m$ Analysis for β-D-2'-deoxyribonucleoside, 4'-$CH_2$—O-2'-BNA, 6'-(S)—$CH_3$—BNA or 2'-(R)-Sulfoxide-BNA In accordance with the present invention, oligomeric compounds were synthesized and Tm's were assessed as illustrated in Example 31 using 4 µM β-D-2'-deoxyribonucleoside, 4'-$CH_2$—O-2'-BNA, 6'-(S)—$CH_3$—BNA or 2'-(R)-Sulfoxide-BNA modified oligomers and 4 µM RNA complement 5'-AGCAAAAAACGC-3' (SEQ ID NO: 5)

| SEQ ID NO./<br>ISIS NO. | Composition<br>(5' to 3') | Tm<br>(° C.) | ΔTm/mod<br>(° C.) |
|---|---|---|---|
| 06/438705 | GCGTTTTTTGCT | 45.4 | — |
| 06/438707 | GCGTTT$_1$TTTGCT | 50.4 | 4.6 |
| 06/438709 | GCGTTT$_S$TTTGCT | 50.5 | 4.7 |
| 06/462886 | GCGTTT$_R$TTTGCT | 49.2 | 3.8 |

Each internucleoside linkage is a phosphodiester. Italicized nucleosides are β-D-ribonucleosides, non-italicized nucleosides not followed by a subscript are β-D-2'-deoxyribonucleosides, subscript 1 indicates that the preceding nucleoside is 4'-$CH_2$—O-2'-BNA, subscript S indicates that the preceding nucleoside is 6'-(S)—$CH_3$—BNA, subscript R indicates that the preceding nucleoside is 2'-(R)-Sulfoxide-BNA (structures drawn below). S indicates the configuration at carbon 6 position of 6-(S)—$CH_3$—BNA. R indicates the configuration of the sulfoxide at carbon 2 position of 2'-(R)-Sulfoxide-BNA.

subscript 1

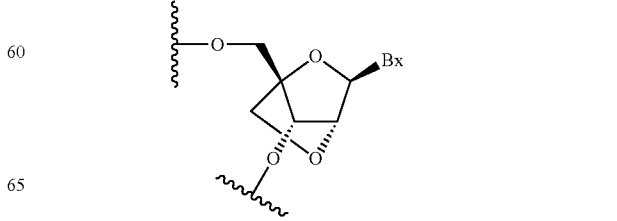

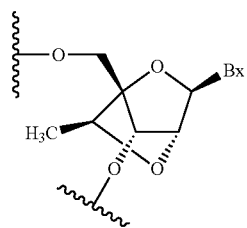 subscript S

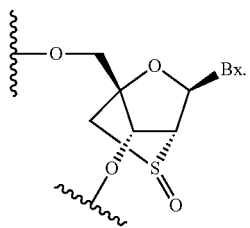 subscript R

---

What is claimed is:

1. A bicyclic nucleoside having Formula Ia:

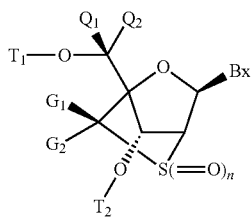

Ia wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
n is 1 or 2.

2. The bicyclic nucleoside of claim 1 wherein Bx is an optionally protected pyrimidine, substituted pyrimidine, purine or substituted purine.

3. The bicyclic nucleoside of claim 2 wherein Bx is uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine.

4. The bicyclic nucleoside of claim 1 wherein at least one of $Q_1$, $Q_2$, $G_1$ and $G_2$ is $CH_3$ and the remaining of $Q_1$, $Q_2$, $G_1$ and $G_2$ are each H.

5. The bicyclic nucleoside of claim 1 wherein $Q_1$, $Q_2$, $G_1$ and $G_2$ are each H.

6. The bicyclic nucleoside of claim 1 wherein $T_1$ is 4,4'-dimethoxytrityl and $T_2$ is diisopropylcyanoethoxy phosphoramidite.

7. The bicyclic nucleoside of claim 1 wherein n is 1 and the configuration at the sulfur atom is R.

8. The bicyclic nucleoside of claim 1 wherein n is 1 and the configuration at the sulfur atom is S.

9. The bicyclic nucleoside of claim 1 wherein n is 2.

10. The bicyclic nucleoside of claim 1 wherein $Q_1$, $Q_2$, $G_1$ and $G_2$ are each H, $T_1$ is 4,4'-dimethoxytrityl and $T_2$ is diisopropylcyanoethoxy phosphoramidite.

11. An oligomeric compound comprising at least one bicyclic nucleoside of Formula IIa:

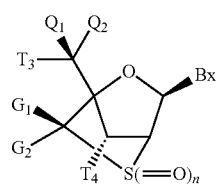

IIa wherein independently for each bicyclic nucleoside of Formula IIa:

Bx is a heterocyclic base moiety;

one of $T_3$ and $T_4$ is an internucleoside linking group attaching the bicyclic nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the bicyclic nucleoside to the remainder of the other of the 5' or 3' end of the oligomeric compound;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;

n is 1 or 2; and wherein said oligomeric compound comprises from 8 to 40 monomeric subunits linked by internucleoside linking groups and wherein at least some of the heterocyclic base moieties are capable of hybridizing to a nucleic acid molecule.

12. The oligomeric compound of claim 11 wherein each Bx is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine.

13. The oligomeric compound of claim 11 comprising at least one 5' or 3'-conjugate group.

14. The oligomeric compound of claim 11 wherein at least one of $Q_1$, $Q_2$, $G_1$ and $G_2$ is $CH_3$ and the remaining of $Q_1$, $Q_2$, $G_1$ and $G_2$ are each H for each bicyclic nucleoside of Formula IIa.

15. The oligomeric compound of claim 11 wherein $Q_1$, $Q_2$, $G_1$ and $G_2$ are each H for each is bicyclic nucleoside of Formula IIa.

16. The oligomeric compound of claim 11 wherein n is 1 and the configuration at the sulfur atom is R for each bicyclic nucleoside of Formula IIa.

17. The oligomeric compound of claim 11 wherein n is 1 and the configuration at the sulfur atom is S for each bicyclic nucleoside of Formula IIa.

18. The oligomeric compound of claim 11 wherein n is 2 for each bicyclic nucleoside of Formula IIa.

19. The oligomeric compound of claim 11 comprising from about 8 to about 20 linked monomer subunits.

20. The oligomeric compound of claim 11 comprising a gapped oligomeric compound comprising a first region consisting of from 2 to 5 modified nucleosides, a second region consisting of from 2 to 5 modified nucleosides and a gap region located between the first and second regions, wherein at least one of the modified nucleosides of the first and second region is a bicyclic nucleoside having Formula IIa and wherein each monomer subunit in the gap region is independently, a nucleoside or a modified nucleoside that is different from each bicyclic nucleoside of Formula IIa and each of the modified nucleosides in the first and second regions.

21. The oligomeric compound of claim 20 wherein the gap region comprises from about 8 to about 14 contiguous β-D-2'-deoxyribonucleosides.

22. The oligomeric compound of claim 20 wherein essentially each modified nucleoside of the first and second region is a bicyclic nucleoside having Formula IIa.

23. The oligomeric compound of claim 20 wherein each of the modified nucleosides that is other than a bicyclic nucleoside having Formula II is, independently, a substituted nucleoside having one or more sugar substituent groups, an optionally substituted 4'-S nucleoside or an optionally substituted bicyclic nucleoside.

24. The oligomeric compound of claim 11 wherein each internucleoside linking group is, independently, a phosphodiester internucleoside linking group or a phosphorothioate internucleoside linking group.

25. The oligomeric compound of claim 11 wherein essentially each internucleoside linking group is a phosphorothioate internucleoside linking group.

26. A method of inhibiting gene expression comprising contacting a cell with an oligomeric compound of claim 11 wherein said oligomeric compound is complementary to a target RNA.

* * * * *